(12) United States Patent
Perkins et al.

(10) Patent No.: US 6,500,461 B2
(45) Date of Patent: *Dec. 31, 2002

(54) PARTICULATE FORMULATIONS

(75) Inventors: Walter Perkins, Trenton, NJ (US);
Xingong Li, Levittown, PA (US);
Donald Hirsh, Trenton, NJ (US); Eric
Mayhew, Monmouth Junction, NJ (US);
Imran Ahmad, Cranbury, NJ (US);
Shaukat Ali, Monmouth Junction, NJ
(US); Andrew Janoff, Yardley, PA (US)

(73) Assignee: The Liposome Company, Princeton, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,338

(22) Filed: May 19, 1999

(65) Prior Publication Data
US 2002/0034536 A1 Mar. 21, 2002

Related U.S. Application Data
(60) Provisional application No. 60/086,108, filed on May 20, 1998.

(51) Int. Cl.⁷ .................................................. A61K 9/14

(52) U.S. Cl. .................. 424/489; 424/427; 424/434; 424/435; 424/436; 424/490; 264/4.1; 264/4.3; 264/4.6

(58) Field of Search .................. 424/450, 1.21, 424/9.321, 9.51, 417, 94.3, 489–502, 427, 434–436, 449; 436/829; 264/4.1, 4.3, 4.6

(56) References Cited

U.S. PATENT DOCUMENTS

| 5,346,702 A | * | 9/1994 | Na .............................. 424/490 |
| 5,415,867 A | * | 5/1995 | Minchey ..................... 424/450 |
| 5,415,869 A | | 5/1995 | Straubinger et al. ........ 424/450 |
| 5,439,686 A | | 8/1995 | Desai et al. ................. 424/451 |
| 5,478,860 A | | 12/1995 | Wheeler et al. ............. 514/449 |
| 5,578,325 A | * | 11/1996 | Domb ......................... 424/501 |
| 5,599,556 A | | 2/1997 | Meyer et al. |
| 5,776,486 A | | 7/1998 | Castor et al. ............... 424/450 |

FOREIGN PATENT DOCUMENTS

| GB | 2 185 397 A | 7/1987 |
| WO | 91/19486 | 12/1991 |
| WO | 94/03160 | 2/1994 |
| WO | 98/13029 | 4/1998 |

OTHER PUBLICATIONS

Hristova in Macromolecules. 28, p. 7693, 1995.*
Alkan–Onyuksel, et al., "A Mixed Micellar Formulation suitable for the Parenteral Administration of Taxol," Pharmaceutical Res. (1994), 206–212.
Chen, et al. "Microdetermination of Phosphorus", Anal. Chem., 28 (11), (1956), 1756–1758.

(List continued on next page.)

Primary Examiner—Gollamudi S. Kishore
(74) Attorney, Agent, or Firm—Burns, Doane, Swecker & Mathis, L.L.P.

(57) ABSTRACT

This invention provides vehicles capable of delivering high concentrations of poorly hydrophilic/poorly lipophilic compounds to animals, by combining compounds having biocompatible hydrophobic domains with conjugates having both hydrophobic and hydrophilic regions. Such formulations are suitable for a number of uses in animals, particularly the administration thereto of high concentrations of therapeutically useful compound, without an undue level of side effects.

52 Claims, 25 Drawing Sheets

OTHER PUBLICATIONS

Perkins et al., "The determination of liposome captured volume," Chemistry and Physics of Lipids, 64, (1993), 197–217.

Kwon, G. et al; "Block Copolymer Micelles for Drug Delivery: Loading and Release of Doxorubicin", Journal of Controlled Release, Elsevier Science Publishers B.V. Amsterdam, NL, vol. 48, No. 2–3, Oct. 13, 1997, pp. 195–201 XP004125856.

Yokoyama, M. et al; "Improved Synthesis of Adriamycin–Conjugated Poly(Ethylene Oxide)–Poly(Aspartic Acid) Block Copolymer and Formation of Unimodal Micellar Structure with Controlled Amount of Physically Entrapped Adriamycin"; Journal of Controlled Release, Elsevier Science Publishers B.V. Amsterdam, NL, vol. 32, No. 3, Dec. 1, 1994, pp. 269–277, XP004037660.

* cited by examiner

PARTICULATE FORMULATIONS

This application claims priority over the provisional application No. 60/086,108 dated Apr. 20, 1998.

FIELD OF THE INVENTION

Particles containing high concentrations of compounds available for therapeutic, diagnostic or other use are provided herein.

BACKGROUND OF THE INVENTION

Effective use of potentially beneficial compounds requires the ability to deliver compositions containing useful levels of the compounds without an undue level of side effects. A variety of vehicles exist in which both hydrophilic and lipophilic compounds can be solubilized at useful levels of the compounds, and then effectively administered. However, there has heretofore been a lack of delivery vehicles in which poorly hydrophilic/poorly lipophilic compounds, such as various taxanes, vinca alkaloids, cephalosporins and steroids, can be effectively used.

One such compound is the taxane paclitaxel, a poorly hydrophilic/poorly lipophilic molecule insufficiently soluble in the more commonly used pharmaceutical carriers to make therapeutically useful compositions thereof. Rather, paclitaxel (Taxol®) is currently made available in the cremophor/ethanol vehicle Cremophor®EL. However, this composition may have certain undesirable side effects at the concentrations administered to provide effective therapeutic levels of paclitaxel, e.g., acute toxicities, exhibited in some patients to whom the composition has been administered (see, e.g., Straubinger et al., U.S. Pat. No. 5,415,869).

Straubinger et al. (see U.S. Pat. No. 5,415,869), for example, formulates paclitaxel in liposomes, and at a limited ratio of paclitaxel to liposomal lipid. Moreover, Straubinger's maximum concentration of paclitaxel is (see Abstract) significantly below the level at which the drug is accumulated in this invention's particles. Furthermore, Desai et al. (U.S. Pat. No. 5,439,686), Wheeler (U.S. Pat. No. 5,478,860) and Alkan-Onyuksel et al. (Pharmaceutical Res. (1994), pp. 206–212) each also encompass compounds in their vehicles at low compound:vehicle component ratios, and at concentrations less than those at which the compounds can be accumulated in the vehicles provide herein.

This invention provides a vehicle for solubilizing poorly hydrophilic/poorly lipophilic compounds, e.g., paclitaxel, such that the resulting compositions can be used to safely administer high doses of the compounds, without an undue level of side effects. This invention's particle, which contains the compound at a high ratio of compound to other vehicle components, is neither a liposome nor an emulsion particle, and has not previously been described.

SUMMARY OF THE INVENTION

This invention provides a particle composed of a core surrounded by a hydrophilic/hydrophobic conjugate. The core comprises poorly hydrophilic/poorly lipophilic compounds for example, taxanes, vinca alkaloids, bryostatins, cyclic polypeptides such as cephalosporins, steroidal compounds, rifamycins, mitomycins, bleomycins, benzonaphthopyranone, bisintercalating antibiotics, nucleoside antibiotics, pyrrolo[1,4]benzodiazepines, macrolides, including macrolide antibiotics such as hamycin, bisindolealkaloids, camptothecins, etoposides, teniposides, DNA intercalators, antiestrogens, bis(benzimidazoles) and nucleosides such as adenine arabinoside. Such compounds have a biocompatible hydrophobic domain, e.g., an acyl chain, hydrophobic peptide or hydrophobic polymer chain, either naturally occurring therein or linked thereto by synthetic means. Alternatively the core could comprise a hydrophilic compound to which a hydrophobic domain has been conjugated such that the net result is that the core composition is poorly hydrophilic.

The conjugate surrounding the core comprises a biocompatible hydrophobic domain linked to a biocompatible hydrophilic domain. The conjugate may be a naturally occurring or synthetic molecule having a hydrophobic and hydrophilic domain or may be a conjugate of a hydrophobic and a hydrophilic domain. Suitable conjugate hydrophobic domains include, for example, the acyl chain regions of amphipathic lipids, as well as hydrophobic polymers such as silicon polymers and hydrophobic peptides. Suitable hydrophilic domains include, for example, polyethylene glycols, celluloses, hydrophilic peptides, polysaccharides, polyethylene oxides, polyacrylic acids, polyacrylamides, polyvinyl pyrrolidinones and polymethacrylates. Suitable hydrophilic domains also include the polar headgroups of amphipathic lipids; these generally are positively or negatively charged, and include phosphatidylserines, phosphatidylglycerols and phosphatidic acids, as well as other lipids, e.g., phosphatidylethanolamines, to which organic dicarboxylic acids, e.g., glutaric acid, are attached.

Preferably, the core compound is a taxane having attached thereto a 10–24 carbon-long, straight, saturated acyl chain, the conjugate hydrophobic domain is a phosphatidylethanolamine, and the conjugate hydrophilic domain is a hydrophilic polymer such as polyethylene glycol of 50–5000 molecular weight. Most preferably, the core compound is paclitaxel attached to a 12, 14 or 16 carbon-long, straight, saturated, alpha-carbon bromylated acyl chain, the conjugate hydrophilic domain is distearoyl phosphatidylethanolamine ("DSPE"), and the conjugate hydrophilic domain is 2000 molecular weight polyethylene glycol ("PEG$_{2000}$").

Compositions containing such particles suspended in pharmaceutically acceptable carriers are also provided herein. These compositions can be used for highly efficient delivery of compounds to animals, i.e., for delivery at high ratios of the compounds to other components of the particles. Such delivery is also at lower toxicities than obtained with currently available formulations of similar compounds. Said high efficiency/low toxicity formulations can be used to administer agents to animals such as humans, for therapeutic, diagnostic or other purposes, e.g., for the treatment of various cancers.

Other features, objects and advantages of the invention and its preferred embodiments wll become apparent from the detailed description which follows.

DETAILED DESCRIPTION OF THE INVENTION

Figure 1A:
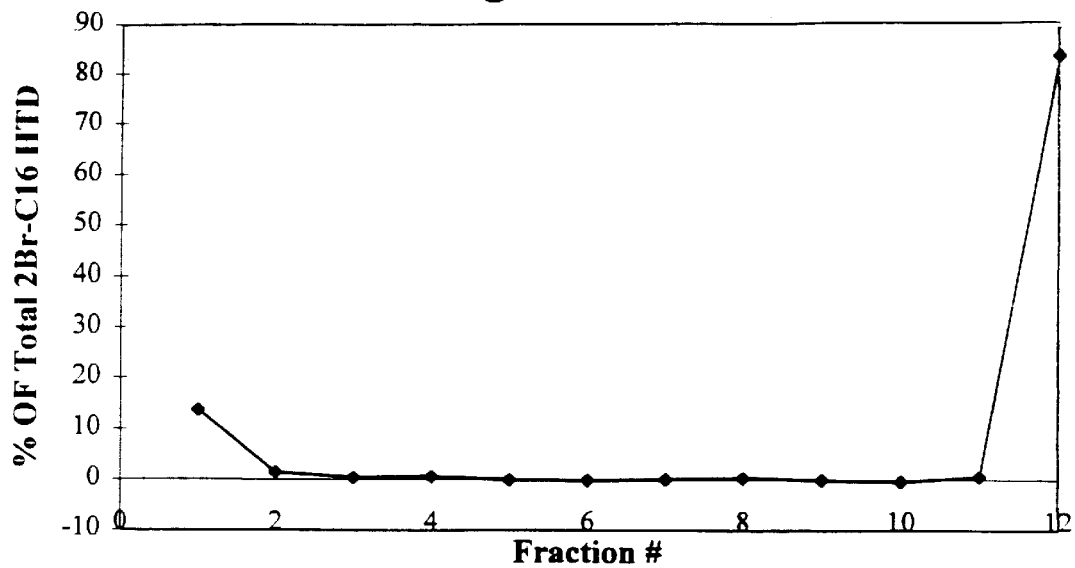
FIGS. 1A–1B. Sucrose-Gradient Fractionation of a Preparation Containing DOPC, DOPE-PEG$_{2000}$ and BrC16-Paclitaxel (30:50:20 respective molar ratio). X-axes: fraction #; y-axis: A: % of total paclitaxel present in sample; B: phospholipid concentration (mM).

Following are acronyms and abbreviations used throughout the application, as well as the corresponding words, phrases or formulas: Br: Bromine; BrC6: —C(O)CHBr(CH$_2$)$_3$CH$_3$; BrC8: —C(O)CHBr(CH$_2$)$_5$CH$_3$; BrC12: —C(O)CHBr(CH$_2$)$_9$CH$_3$; BrC14: —C(O)CHBr(CH$_2$)$_{11}$CH$_3$; BrC16 —C(O)CHBr(CH$_2$)$_{13}$CH$_3$; HTD: hydrophobic taxane (such as paclitaxel) derivative; BrC16HTD: paclitaxel covalently attached to a 16-carbon, straight-chained, saturated, alpha-carbon bromylated acyl chain; DOPC: dioleoyl phosphatidylcholine; DMPE: dimyristoyl phosphatidylethanolamine; DOPE: dioleoyl phosphatidylethanolamine; DPPE: dipalmitoyl phosphatidylethanolamine; DSPE: distearoyl phosphatidylethanolamine; PEG: polyethyleneglycol; PEG$_{2000}$: PEG with a molecular weight of about 2000; PEG$_{5000}$: PEG with a molecular weight of about 5000. Moreover, concentrations of compounds in this invention's particles are described herein in ratios of the mole percentage of each component in the particle (for example, BrC16-paclitaxel/DSPE-PEG$_{2000}$ (85:15) is a particle containing paclitaxel covalently attached to a 16 carbon-long, alpha-carbon bromylated acyl chain, and distearoyl phosphatidylethanolamine-2000 molecular weight polyethylene glycol, at a respective ratio of 85 mole % of the paclitaxel/acyl chain to 15 mole % of the DSPE-PEG$_{2000}$).

This invention provides a particle composed of a poorly hydrophilic core, surrounded by a biocompatible hydrophobic domain/biocompatible hydrophilic domain conjugate. The hydrophobic core compounds of the present invention are poorly hydrophilic and, when placed in an aqueous environment will self associate. The hydrophobic core compounds may be naturally occurring hydrophobic compounds or synthetic hydrophobic compounds. In addition, the core hydrophobic compounds may be hydrophobic or poorly lipophilic derivatives of any compound. For instance, a hydrophilic compound may be derivatized with a hydrophobic domain to form a compound that is poorly hydrophilic. In one embodiment, hydrophobic compound may comprise the hydrophilic compound arabinosyl cytosine (Ara C) derivatized with a hydrophobic domain domain to form a core compound that is hydrophobic. Compounds of interest are contained within the cores of the particles at levels significantly higher than those at which similar compounds have previously been made available within carrier particles. Such core compounds include, for example and without limitation: taxanes, e.g., paclitaxel; vinca alkaloids, e.g., vinblastine; bryostatins; cyclic polypeptides such as cephalosporins; other hydrophobic polypeptides, steroidal compounds, e.g., prednisone and cortisone; rifamycins, e.g., rifabutin and rifamide; mitomycins; bleomycins; benzonaphthopyranones; bisintercalating antibiotics, e.g., quinomycin; nucleoside antibiotics, e.g., ara-a; pyrrolo[1,4] benzodiazepines, e.g., anthramycin and distamycin; macrolides, e.g., maytansine and hamycin; bisindolealkaloids, e.g., vinblastine and navelbine; camptothecins and camptothecin analogs; etoposide and teniposide; DNA intercalators, e.g., amsacrine; antiestrogens, e.g., tamoxifens; bis(benzimidazoles) such as Hoechst 33258; and, hydrophobic peptides, particularly hydrophobic peptides with attached acyl chains (e.g., surfactant peptides.

Such compounds have a biocompatible hydrophobic domain; said domain is safely administered to animals at therapeutic levels, and increases the compound's hydrophobicity sufficiently to allow it to accumulate at high levels (i.e., at about 20 mole % or greater) within the particle. The domain is either naturally occurring in the compound, e.g., bryostatins, or is synthetically conjugated thereto, e.g., taxanes such as paclitaxel. Preferably, the core compound has a conjugated biocompatible hydrophobic domain, "conjugated" meaning the covalent attachment of the domain to a reactive moiety on the compound by synthetic chemical reactions.

Preferably, the core compound is a taxane such as paclitaxel, taxotere, cephalomannine, 19-hydroxy baccatin III, baccatin III, 10-deacetyl cephalomannine, 10-deacetyl taxol (7α-OH), epi-10- deacetyl taxol (7β-OH), 7-Epi-10-deacetyl cephalomannine (7β-OH) and 10-deacetyl baccatin III. Most preferably, the core compound is paclitaxel.

Attachment of biocompatible hydrophobic domains to such compounds is accomplished by known means of attaching moieties such as acyl chains, hydrophobic peptides and silicon polymers to other compounds. For example, where the hydrophobic domain is an acyl chain, the preferred means of attachment is by establishing a bond between the carboxyl group of the acyl chain and a hydroxyl group on the compound, e.g., paclitaxel, camptothecin or vinblastine.

Taxanes such as paclitaxel, for example, have hydroxyl groups (e.g., 2' and 7 OH groups) to which hydrophobic domains can be attached. As the relative order of reactivity of these groups is generally believed to be (from most reactive to least reactive) 2'>7, an acyl chain can be attached to taxanes at the 2' position using a stoichiometric amount of a reactive form of the chain. e.g., the chloride or anhydride form. Alternatively, acyl chains are attached to both the 2' and 7 OH groups, and then selectively removed from the 2' acyl chain so that only the chain at the 7 position remains attached to the taxane. Selective removal of the 2' acyl chain can be accomplished using stoichiometric amounts of a mild base, e.g., sodium bicarbonate. Additionally, the 7 OH group can be modified by first "protecting" the 2' OH group with moieties such as triphenyl methyl, methoxytriphenyl methyl, trifluoroacetyl and TrOC (trichloromethoxy chloroformate) groups, using processes generally known to ordinarily skilled artisans. The protected taxane is then reacted with an active form of the acyl chain, e.g., anhydrides or chlorides, in anhydrous organic solvent with bases such as DMAP and pyridine; the protecting group is subsequently removed from the 2' position by well known and readily practiced means. Such reactions are typically performed in the presence of a base, such as pyridine, dimethylaminopyridine ("DMAP"), triethylamine, or others, and in common polar, aprotic organic solvents such as methylene chloride, formamide, chloroform, THF (tetrahydrofuran), dimethyl formamide and dimethyl sulfoxide (DMSO).

Hydrophobic domains suitable for attachment to such compounds include, for example and without limitation, acyl chains, hydrophobic peptides, silicon chains and other hydrophobic polymers. Preferably, the hydrophobic domain is an acyl chain, branched or straight, saturated or unsaturated and alpha-carbon bromylated or unbromylated. More preferably, the conjugated hydrophobic domain is an acyl chain having the formula $-C(O)CHX^1(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}CH_3$, wherein: n1 is equal to zero or is an integer of from 1 to 21; n3 is equal to zero or is an integer of from 1 to 18; n5 is equal to zero or is an integer of from 1 to 15; n7 is equal to zero or an integer of from 1 to 12; n9 is equal to zero or is an integer of from 1 to 9; and, each of n2, n4, n6 and n8 is independently equal to 0 or 1. The sum of n1+2n2+n3+2n4+n5+2n6+n7+2n8+n9 is an integer equal to from 3 to 21. More preferably, the acyl chain is straight-chained, saturated and 12, 14 or 16 carbons in length, i.e., -is $C(O)CHX^1(CH)_9CH_3$, $-C(O)CHX^1(CH)_{11}CH_3$, or $-C(O)CHX^1(CH)_{13}CH_3$.

$X^1$ of such acyl chains is either H or, more preferably, a "hydrolysis promoting group" ("HPG"), i.e., an atom or set thereof which promotes the in vivo hydrolysis of its parent chain from the compound to which it is attached. HPGs are electronegative relative to hydrogen, meaning that they draw electrons to themselves more than a hydrogen atom would if it occupied the same position in the same molecule. Accordingly, substitution of an HPG for a hydrogen atom on the alpha carbon of the acyl chain results in a redistribution of the chain's electron density, leading to an inductive effect in the chain. Furthermore, substitution of aromatic moiety-containing HPGs for acyl chain alpha carbon hydrogens can cause electron density-redistributing resonance effects. Such HPG-induced induction and resonance effects stabilize an acid's corresponding base form, but not the acid form. Hence, the acid is a stronger acid than would be the case if there was an H at the position of the acyl chain instead occupied by the HPG. Acyl chains modified by HPGs thus generally have lower $pK_a$'s than their corresponding native forms, that is, the form in which a $CH_2$ group is present at the alpha position instead of an HPG-substituted group. Hence, HPG-substituted acyl chains are more readily hydrolyzable in vivo from parent compounds than are the native chains.

The hydrolysis-promoting group $X^1$ is any atom or group of atoms: (1) having an electronegativity greater than hydrogen; and, (2) that can be attached at the alpha position of an acyl chain. Such groups include, for example and without limitation, F, Cl, Br, I, $NH_3^+$, $-OC_6H_4X^2$, or $-C(O)X^2$, wherein $X^2$ is, for example, F, Cl, Br, I, $NH_3^+$, $NO_2$ or CN. Preferably, $X^1$ is F, Cl, Br or I, most preferably, Br. Acyl chains most preferred for attachment to compounds herein are thus $-C(O)CHBr(CH_2)_9CH_3$, $-C(O)CHBr(CH_2)_{11}CH_3$, or $-C(O)CHBr(CH_2)_{13}CH_3$. HPG-substituted acyl chains can be purchased commercially, or can be made by any of the means generally accepted in the art for making substitutions on the alpha carbons of acyl chains.

The conjugate around the core is composed of linked hydrophilic and hydrophobic domains. The conjugate may be a natural or synthetic lipid having a hydrophobic and hydrophilic domain. Alternately, the conjugate may be a synthetic compound having a hydrophilic domain linked to a hydrophobic domain by chemical means. Suitable conjugate hydrophilic domains are those which are: 1) biocompatible, i.e. can be administered to animals without an undue level of side effects; 2) overall more hydrophilic than hydrophobic; and, 3) capable of attachment to a hydrophobic domain. These include, for example and without limitation: cellulose; polyethylene glycols; polyaminoacids, e.g., polyglycine; polysaccharides; poly(ethylene oxides); poly(acrylic acids); poly(acrylamides); poly(vinyl pyrrolidinones); and, poly(methacrylates). Where the hydrophilic domain is a hydrophilic polymer, the polymer is preferably a polyethylene glycol ("PEG") or a polyoxyethylene, more preferably, a PEG or polyoxyethylene having a molecular weight of from about 50 to about 5000, and most preferably, PEG having a molecular weight of about 2000 ("PEG$_{2000}$"). The hydrophilic domain can also be the polar headgroup region of an amphipathic lipid. Said headgroups can bear a charge, either positive or negative; the charge can either be naturally occurring on the headgroup, or added thereto via linkage of a charged molecule to a reactive moiety on the headgroup. Charged lipids include, for example and without limitation, phosphatidylserines, phosphatidylglycerols, phosphatidic acids, and phosphatidylethanolamines to which organic dicarboxylic acids, e.g., glutaric, oxalic and succinic acids, have been attached.

Suitable conjugate hydrophobic domains are those which: 1) are biocompatible; 2) have a moiety capable of attachment to a hydrophilic domain; and, 3) overall are more hydrophobic than hydrophilic. Such domains include, without limitation, the acyl chain regions of amphipathic lipids, various hydrophobic polymers such as silicon polymers and hydrophobic peptides.

Amphipathic lipid headgroups are hydrophilic, hence, the lipids themselves are hydrophobic/hydrophilic conjugates. Such lipid conjugates generally bear a charge, positive or negative, on the headgroup, and include phosphatidylserines (PS's), phosphatidylglycerols (PGs) and phosphatidic acids ("PAs). Alternatively, the headgroups have reactive moieties to which further hydrophilic domains are attached. Such lipids preferably are phosphatidylethanolamines ("PEs"), such as dipalmitoyl phosphatidylethanolamine ("DPPE"), palmitoyloleoyl phosphatidylethanolamine ("POPE"), dioleoyl phosphatidylethanolamine ("DOPE") or distearoyl phosphatidylethanolamine ("DSPE"); more preferably, the phosphatidylethanolamine is DSPE.

Amphipathic lipid-containing conjugates thus include conjugates of PEs and PEG; these preferably are conjugates of DSPE and PEG of 50–5000 molecular weight, and most preferably, DSPE-PEG$_{2000}$. Amphipathic lipid-containing conjugates also include various charged lipids, such as the phosphatidylethanolamine-dicarboxylic acids DOPE-GA and POPE-GA ("GA"=glutaric acid).

Biocompatible hydrophilic/hydrophobic conjugates are also hydrophilic/hydrophobic copolymers, such as a copolymer having the formula HO(CH$_2$CH$_2$O)$_a$(CH(CH$_3$)CH$_2$O)$_b$(CH$_2$CH$_2$O)$_c$H. More preferably, in such polyoxyethylene-polyoxypropylene copolymers, a and b are each independently equal to integers of from about 10 to about 100, and c is equal to zero or is an integer of from about 1 to about 100. Most preferably, a and c are each equal to 75, and b is equal to 30.

Hydrophobic domain-containing core compounds comprise from about 20 mole % to about 99 mole % of the particle, and can comprise any amount in between, e.g., from at least about 25, 30, 35, 40, 45, 50, 55, 60, 65, 70, 75, 80, 85, 90 or 95 mole % to about 99 mole %. Hydrophobic domain-hydrophilic domain conjugates comprise from about 1 mole % to about 80 mole % of the particle, and can comprise any amount in between, e.g., from about 80 mole % to about 75, 70, 65, 60, 55, 50, 45, 40, 35, 30, 25, 20, 15, 10, 5 or 1 mole %. Most preferably, presently, the core compounds comprise about 80–99 mole % of the particle, while the conjugates comprise about 1–20 mole % of the particle.

Core compounds, because of their hydrophobic domains, accumulate at high concentrations, in association with the surrounding conjugate, within the particles provided herein. Said high level accumulation does not require the presence of, and occurs in the absence of, such additional components as oil or water in the core; the cores of this invention's particles are thus substantially free of water and added oil. Absent the hydrophobic domain, the compounds could not accumulate in carriers, e.g., liposomes or emulsions, without the use of oil or water, or at the levels at which compounds are contained in the cores of this invention's particles.

Hence, the particles of this invention are neither liposomes, which have aqueous volume entrapped within lipid bilayers. nor emulsions, which have either an oil-in-water, or a water-in-oil organization, i.e., globules of one liquid within another. Rather, this invention's particles are substantially different from such structures, said differences being readily demonstrable by ordinarily skilled artisans using well known methods. These include: assessing the concentration of core compound within a carrier particle, e.g., according to the sedimentation studies set forth in Example 3 hereinbelow; demonstrating the presence or absence of water or added oil within a particle, e.g., by NMR spectroscopy, percentage entrapment of available soluble markers within a particle, measurement of tritiated water distribution, volume distribution by determination of externally added solute, and turbidity measurements based upon the swelling of liposomes in hypo-osmotic environments; and, demonstrating the presence or absence of lipid bilayer organization by freeze-fracture and cryo-electron microscopy, as well as NMR spectroscopic examination of lipid molecular organization.

Particles provided herein are approximately spherical in shape and have diameters, or sizes, of at least about 15 nm, and preferably, no greater than about 10,000 nm, although larger particles are contemplated for nonintravenous use. The particles can be any size in between, but most preferably are about 15–200 nm in size. Particle size is affected by a number of factors within the purview of the artisans to determine, including the relative proportions of derivative and conjugate in a particle, and can be determined according to the following equations:

# of moles poorly hydrophilic compound/particle $(X)$=[density× $(4/3\ \pi)(d/2-t)^3$]/mol. wt. poorly hydrophilic compound;     (1)

moles conjugate/particle $(Y)=(\pi d^2)/(a)\times 6.0225\times 10^{23}$; and,     (2)

mole % poorly hydrophilic compound=$[X/(X+Y)]\cdot 100$,     (3)

where "d" is the particle's diameter, "t" is the thickness of the conjugate layer, "a" is the surface area per molecule of the conjugate component, and "density" is given in g/cm$^3$. Particle size can be measured by a variety of techniques available to ordinarily skilled artisans (including the techniques set forth in Example 5 hereinbelow), Particles of this invention are typically prepared by ethanol injection or reverse-phase evaporation (REV). They can also be prepared by a dialysis method. Briefly, in the ethanol injection procedure (see Example 1 hereinbelow), suitable amounts of the particles' components are dissolved in an appropriate amount of a suitable organic solvent, e.g., ethanol. The resulting ethanolic solution(s) are then slowly injected to an appropriate amount of a suitable aqueous solution (e.g., the buffer HEPES/NaCl pH 7.5) so as to form particles in the buffer; the particles can then be collected following centrifugation. According to the reverse phase evaporation procedure (see Example 1 hereinbelow), suitable amounts of the particles' components are mixed, and then dissolved in an appropriate amount of an aqueous buffer/miscible organic solvent combination, followed by removal of organic solvent under vacuum or under a stream of inert gas.

Particles of this invention can be combined with pharmaceutically acceptable carriers, and thus also provided in the form of pharmaceutical compositions containing the particles and the carriers. "Pharmaceutically acceptable carriers" are those media generally acceptable for use in connection with the administration of therapeutic or diagnostic agents to mammals. Such media are formulated according to a number of factors well within the purview of the ordinarily skilled artisan to determine and account for, including, without limitation: the particular agent being administered, as well as its concentration, stability and intended bioavailability; the disease, disorder or condition being treated or diagnosed with the composition; the subject, its age, size and general condition; and the composition's intended route of administration, e.g., nasal, oral, ophthalmic, topical, transdermal, vaginal, rectal, intrathecal, subcutaneous, intramammary, intraperitoneal, intravenous, intratumoral, intracavitary or intramuscular. Pharmaceutically acceptable carriers can contain additional ingredients, for example those which enhance the stability of the active ingredients included, such as preservatives and anti-oxidants.

Pharmaceutical compositions can be administered to animals, e.g., mammals such as humans, by any of the standard means generally accepted in the art for doing so. Routes of administration, e.g., oral, intravenous, intra-arterial, subcutaneous, intramuscular or intraperitoneal administration, are chosen with regard to a number of factors well within the purview of ordinarily skilled artisans, given the teachings of this invention, to determine and account for. Such factors include, without limitation: the age, body mass and general health of the subject being treated; the intended bioavailability of the drug; the particular form of disease being treated; the carrier used; and, the dose of therapeutic agent administered. Presently, oral and intravenous administration are the preferred means of administering pharmaceutical compositions provided herein. Intraperitoneal administration, in the form of a solid, semi-solid or fluidic particle-containing pharmaceutical composition is also preferred herein.

Particle-containing pharmaceutical compositions are provided herein for oral administration in the solid form, e.g., tablets or capsules, as well as the fluid form, e.g., syrups and suspensions. Particle-containing tablets are any of the standard types of tablets, e.g., round, oval or oblong, coated or uncoated, differing in size or weight, that are generally available for use in the pharmaceutical field, and can contain any of a variety of ingredients, in addition to this invention's particles, generally accepted in the field. Capsules are solid dosage forms in which the particles are contained within a gelatinous shell; such capsules can be prepared at a variety of particle dosage levels. Both hard and soft capsules are provided for herein. Formulation of the particles within such tablets, capsules or other solid dosage forms is well within the purview of ordinarily skilled practitioners in the pharmaceutical field.

Intravenous fluids formulated in pharmaceutical compositions with the particles of this invention are sterile aqueous solutions of chemicals, e.g., sugars, amino acids and electrolytes, that can readily be carried within, and then absorbed into, mammals; in addition to serving as vehicles for administration of active ingredients, such fluids are commonly also used for nutrient and electrolyte replenishment. Commonly used intravenous fluids suited for formulation with this invention's particles include, without limitation, physiological saline and 5%-by-weight of dextrose in water.

Further provided herein are methods of administering compounds to animals, the methods comprising administration of particle-containing pharmaceutical compositions provided herein to the animals. Said methods are highly efficient, i.e., deliver the compounds at high ratios of compound to other components of the particles, and low toxicity inducing. In particular, the methods can be used to deliver therapeutically effective amounts of the compounds to the animals to treat diseases, disorders or conditions amenable to treatment with the compound, such treatment being without undue levels of side effects. In this regard, a "therapeutically effective amount" of a compound is any amount of the compound effective to ameliorate, lessen or prevent a disease, disorder or condition, and typically is at least about 0.01 mg of the compound per kg of body weight of the animal to which the compound is administered. More preferably, a therapeutically effective amount of a compound is from about 0.01 mg of the compound per kg to about 1000 mg/kg. Conditions treatable with compositions provided herein include, for example and without limitation: various cancers, e.g., brain cancers, breast cancers, ovarian cancers, lung cancers, leukemias, lymphomas, melanomas, carcinomas and sarcomas; parasitic diseases, various inflammatory and autoimmune conditions, e.g., arthritis and juvenile diabetes; and various microbial infections. The term microbial infection is meant to include pathological conditions caused by viruses, bacteria, rickettsiae, fungi, prions and the like. Moreover, compositions provided herein can also be used to administer nontherapeutic agents, e.g., diagnostic or nutritional agents, to animals.

This invention will be better understood from the following Examples. However, those of ordinary skill in the art will readily understand that the examples are merely illustrative of the invention as defined in the claims which follow thereafter.

EXAMPLES

Example 1

Particle Preparation

BrC16-paclitaxel/DSPE-PEG$_{2000}$ Preparation by Ethanol Injection.

For preparation by the ethanol injection method, 20 mg of BrC16-paclitaxel and 8.3 mg of DSPE-PEG$_{2000}$ were weighed, mixed and then solubilized by injection into 0.1 ml of ethanol. The resulting ethanolic solutions were then slowly added to a glass vial containing 2 ml of a 10 mM HEPES, 150 mM NaCl buffer, pH 7.5 (HEPES buffer), so as to form a suspension of particles in the buffer.

BrC16-paclitaxel/DSPE-PEG$_{2000}$ Preparation by Reverse-phase Evaporation Process.

For preparation by the reverse-phase evaporation process, 20 mg of BrC16-paclitaxel and 118 mg of DSPE-PEG$_{2000}$ were mixed and then dissolved in 6 ml of ethanol and 2 ml of the HEPES buffer, subsequent to which the ethanol was removed by rotoevaporation so as to form particles.

Hamycin/DSPE-PEG$_{2000}$ Preparation by Reverse-phase Evaporation (REV) Process.

For preparation by a modified REV process, 20mg of the macrolide antibiotic Hamycin and 80 mg of DSPE-PEG$_{2000}$ were co-dissolved in 40 ml of chloroform and methanol (1/1, v/v). Ten ml of physiological saline (about 0.9%) was added to the mixture and the suspension was briefly sonicated (about 10 sec.) in a bath sonicator at room temperature in order to make a relatively homogeneous dispersion. The solvents were then removed using a rotary evaporator at 45° C. The remaining saline solution contained the preparation comprising particles of Hamycin/DSPE-PEG$_{2000}$ at a 20:80 ratio on a weight to weight basis Hamycin/DSPE-PEG$_{2000}$ Preparation by Dialysis Process.

Hamycin particles can also be prepared by a dialysis method. 80 mg Hamycin and 20 mg of DSPE-PEG$_{2000}$ were co-dissolved in 4 ml of DMSO. 1 ml of the solution containing the macrolide hamycin and lipid was dripped into 9 ml of physiological saline (about 0.9%) while vortexing at room temperature. Three ml of the saline/DMSO solution containing the hamycin and lipid were loaded into a Slide-A-Lyzer (10 k molecular weight cut off) and dialyzed against 2 liters of saline overnight at room temperature. At the end of the dialysis period substantially all of the DMSO was removed. Analysis of the particles demonstrated that they comprised hamycin and DSPE-PEG$_{2000}$ at a 80:20 ratio.

Example 2

Sucrose Gradient Centrifugation

Two hundred-microliter samples containing 6.9 mg of PEGylated lipid-hydrophobic drug derivative combinations (e.g., a 30:50:20 molar ratio combination of DOPC, DOPE-PEG$_{2000}$ and BrC16-paclitaxel), prepared according to the reverse-phase evaporation procedure (as set forth in Example 1, hereinabove) were added to the top of a 12-ml 0–50% sucrose gradient, generated using a Biocomp Gradient Master Model 106 (Biocomp Instruments, Inc., (operation parameters: time: 2 min., angle: 81.5°, speed: 19)). Gradients were centrifuged at 208,000 g on a Beckman L5-50 ultracentrifuge overnight, and fractionated 1 ml each from the top.

Figure 1B:
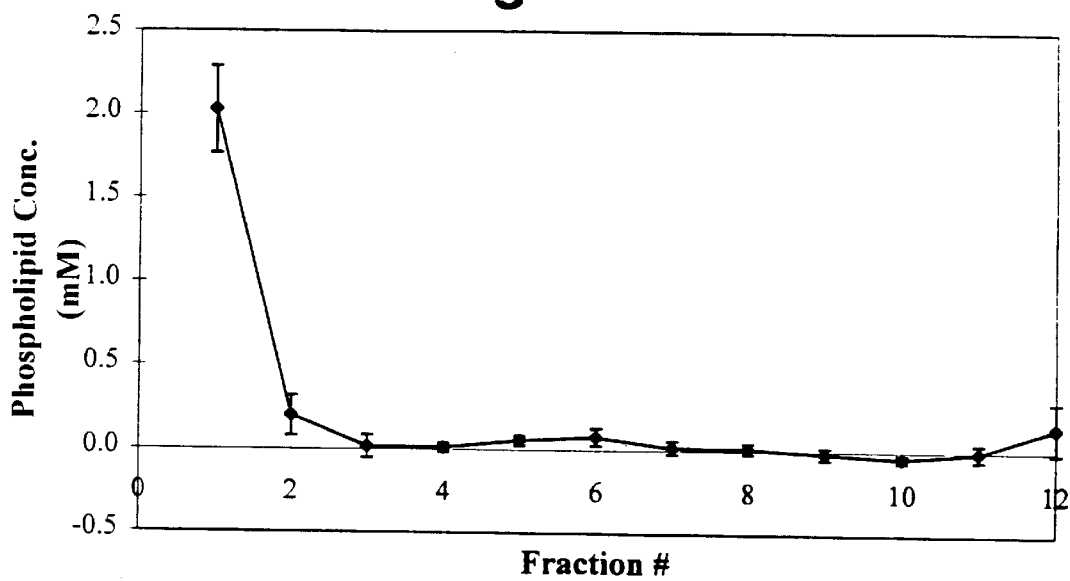

Phospholipid concentrations in the various fractions were determined by a modified version of the procedure of Chen et al (the contents of which are incorporated herein by reference). Compound concentrations were determined by dissolving a sample in ethanol, reading the absorbance in a UV2101PC UV scanning spectrophotometer (Shimadzu Scientific Instruments, Inc.), and then comparing the absorbances with standards. Results are presented in FIGS. 1A and 1B, and are confirmed by light microscopy (as set forth in Example 6 hereinbelow) of the gradient fractions. Particles visible by microscopy were present in the higher density fraction (#12). The mole ratio of BrC16-paclitaxel to phospholipid was 94:6 in fraction 12.

Example 3

Sedimentation Studies

One-ml samples (10 mg/ml BrC16-paclitaxel) of particles prepared by the ethanol injection procedure as set forth in Example 1, hereinabove) were centrifuged at 30,000 g for 30 minutes on a Beckman L5-60 ultracentrifuge; after removal of supernatant, pellets were resuspended in water to approximately the same volume as the samples. Phosphate concentrations in the various fractions were determined by a modified version of the procedure of Chen et al; compound concentrations were determined by dissolving a sample in ethanol, reading the absorbance in a UV2101 PC UV scanning spectrophotometer (Shimadzu Scientific Instruments, Inc.), and then comparing the absorbances with standards. Results of these experiments are presented in Table 1. Typically in the pellet the mole per cent of BrC16-paclitaxel was about 98 mole per cent.

TABLE 1

Sedimentation Studies

| Sample | Fraction Type* | BrC16-Paclitaxel Conc. (mg/ml) | Phosphate Conc. (mM) | Mole % BrC16-Paclitaxel |
|---|---|---|---|---|
| DOPE-PEG$_{2000}$ | 1 | 1.86 | 0.36 | 81.35 |
| DOPE-PEG$_{2000}$ | 2 | 10.39 | 1.33 | 86.95 |
| DOPE-PEG$_{2000}$ | 3 | 7.67 | 0.19 | 97.22 |
| DSPE-PEG$_{2000}$ | 1 | 1.25 | 0.35 | 75.13 |
| DSPE-PEG$_{2000}$ | 2 | 10.93 | 1.29 | 87.90 |
| DSPE-PEG$_{2000}$ | 3 | 8.74 | 0.18 | 97.65 |
| DPPE-PEG$_{2000}$ | 1 | 1.20 | 0.33 | 75.40 |
| DPPE-PEG$_{2000}$ | 2 | 10.77 | 1.26 | 88.00 |
| DPPE-PEG$_{2000}$ | 3 | 9.62 | 0.20 | 97.65 |
| DMPE-PEG$_{2000}$ | 1 | 0.99 | 0.23 | 78.34 |
| DMPE-PEG$_{2000}$ | 2 | 10.43 | 1.13 | 88.78 |
| DMPE-PEG$_{2000}$ | 3 | 9.82 | 0.20 | 97.72 |
| DOPE-PEG$_{5000}$ | 1 | 2.33 | 0.34 | 85.39 |
| DOPE-PEG$_{5000}$ | 2 | 10.15 | 1.04 | 89.27 |
| DOPE-PEG$_{5000}$ | 3 | 4.15 | 0.07 | 98.14 |
| DSPE-PEG$_{5000}$ | 1 | 2.17 | 0.35 | 84.26 |
| DSPE-PEG$_{5000}$ | 2 | 10.13 | 1.10 | 88.77 |
| DSPE-PEG$_{5000}$ | 3 | 4.53 | 0.08 | 98.00 |
| DPPE-PEG$_{5000}$ | 1 | 2.40 | 0.36 | 85.15 |
| DPPE-PEG$_{5000}$ | 2 | 10.21 | 1.11 | 88.77 |
| DPPE-PEG$_{5000}$ | 3 | 3.83 | 0.07 | 98.04 |
| DMPE-PEG$_{5000}$ | 1 | 1.88 | 0.32 | 83.26 |
| DMPE-PEG$_{5000}$ | 2 | 9.97 | 1.09 | 88.68 |
| DMPE-PEG$_{5000}$ | 3 | 4.65 | 0.08 | 98.13 |

*1: Supernatant; 2: whole; 3: pellet.

Example 4

Turbidity Measurements

Having an entrapped aqueous solution, liposomes shrink or swell when placed in medium having a different osmotic strength than that of the solution. Such changes in liposome size in response to osmotic pressure differentials result in a change in the turbidity of a suspension of the liposomes. Particles not having substantial amounts of entrapped aqueous volume, e.g., the particles of this invention, are not subject to the osmotic pressure differentials, and hence, suspensions of the particles do not exhibit significant changes in turbidity.

Figure 2:
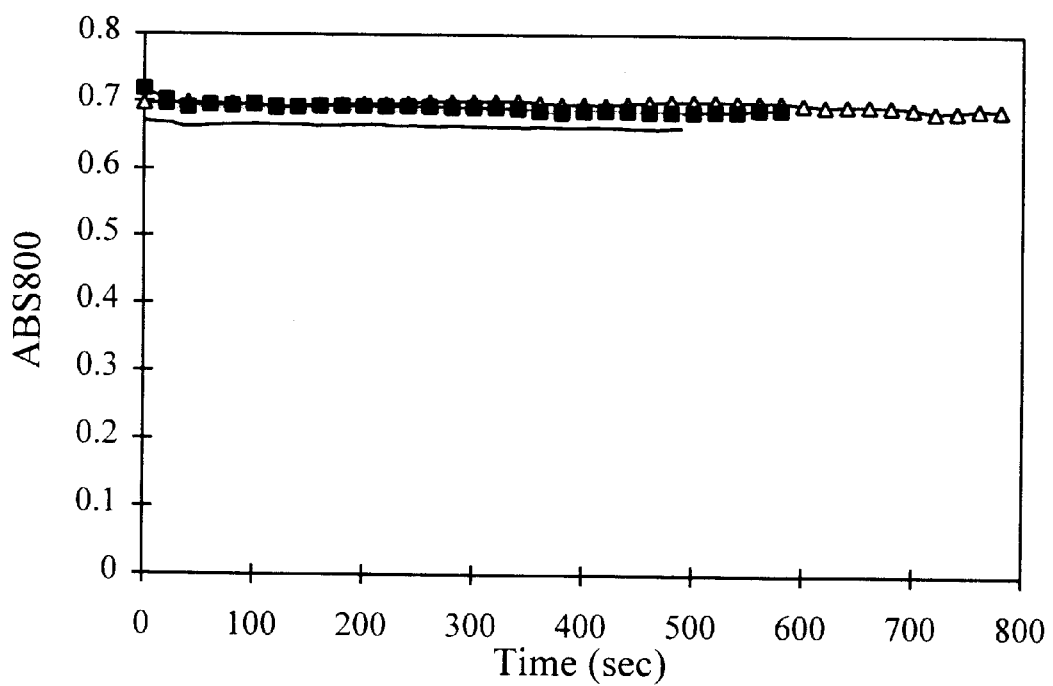
FIG. 2. Turbidity of a Preparation Containing DOPC:DOPE-PEG$_{2000}$:BrC16-Paclitaxel (10:10:80) Diluted in Different Osmotic Strength Solutions. X-axis: time (sec); y-axis: absorbance (800 nanometers). Open triangles: H$_2$O; thin lines: 75 mM NaCl; filled squares: 150 mM NaCl; thick lines: 300 mM NaCl.
Figure 3C:
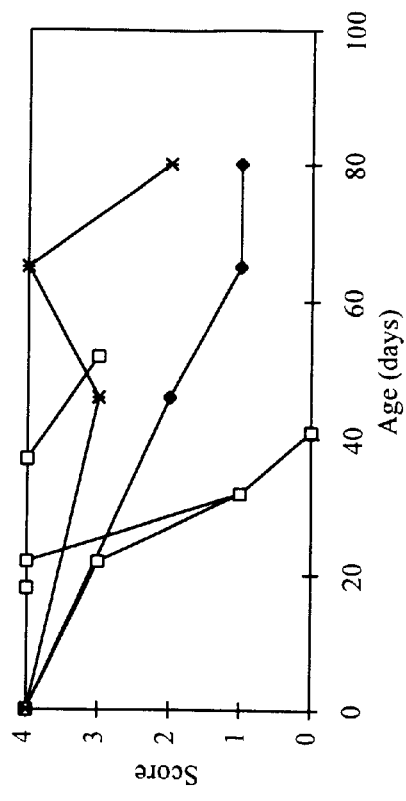
FIGS. 3A–3D. Stability of Preparations Stored at Room Temperature. X-axes: time (days); y-axes: score criteria: 0: +++ crystallization; 1: ++ crystallization; 2: + crystallization; 3: no crystallization, irregularly shaped particles; 4: no crystallization. A: DOPC:DOPE-PEG$_{2000}$:BrC16-Paclitaxel (10:10:80); B: DSPE-PEG$_{2000}$: BrC16-Paclitaxel, 20:80 (filled diamonds) or 10:90 (squares); C: DOPE-PEG$_{2000}$-BrC16-Paclitaxel, 20:80 (filled diamonds), 15:85 (squares) or 10:90 (star); D: PE-PEG$_{2000}$:BrC16-Paclitaxel and PE-PEG$_{5000}$:BrC16-Paclitaxel each at 15:85: DPPE-PEG$_{2000}$- filled diamonds; DOPE-PEG$_{5000}$- squares; DPPE-PEG$_{5000}$- x; DMPE-PEG$_{5000}$- triangles.
Figure 3D:
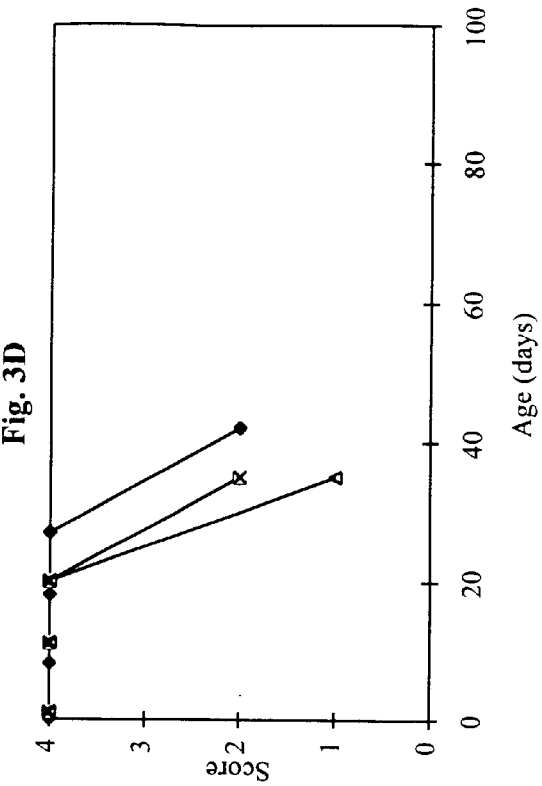
Figure 3A:
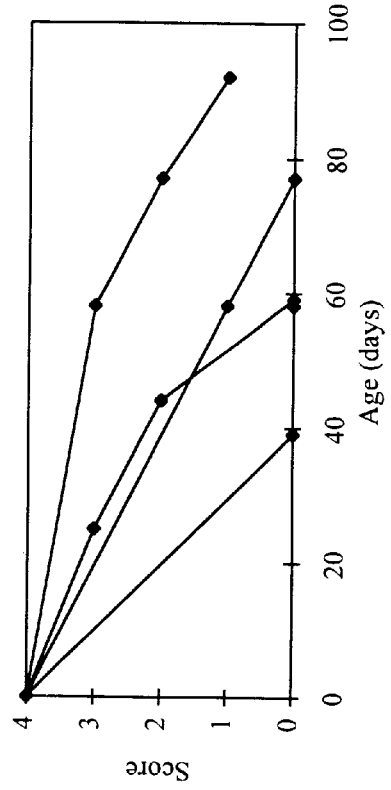
Figure 3B:
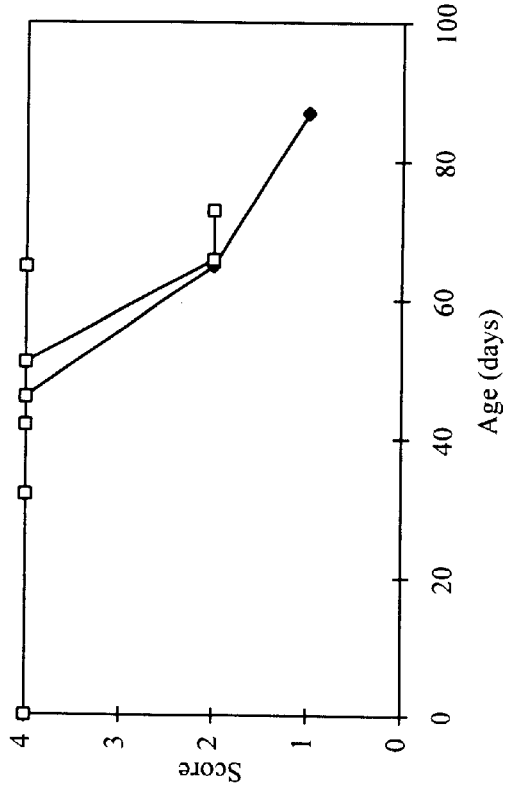
Figure 4C:
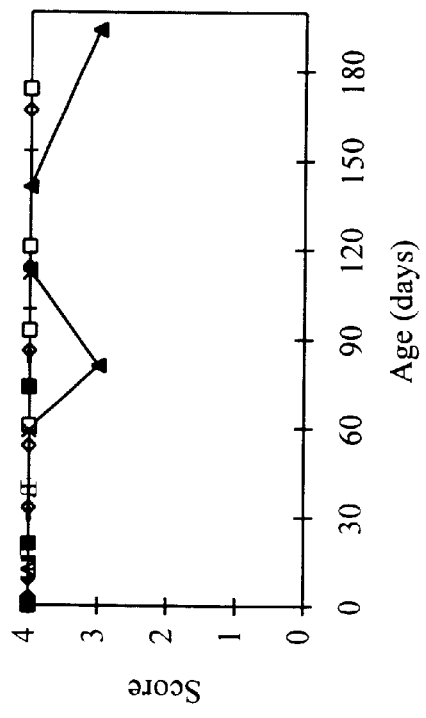
FIGS. 4A–4E. Stability of Formulations (15:85) Stored at 4 Degrees Celsius in the Dark. X-axes: formulation age (days); y-axes: subjective score (see legend to FIG. 3, hereinabove). A: DOPE-PEG$_{2000}$:BrC16-paclitaxel. B: DOPE-PEG$_{5000}$:BrC16-paclitaxel. C: DSPE-PEG$_{2000}$:BrC16-paclitaxel. D: DMPE-PEG$_{5000}$:BrC16 paclitaxel. Formulations prepared at: day X–5 (▲); day X (♦); day X+15 (□); day X+22 (◇). E: BrC16-paclitaxel - containing formulations (15:85): DPPE-PEG$_{2000}$ (♦); DMPE-PEG$_{2000}$ (□); DSPE-PEG$_{5000}$ (Δ); DPPE-PEG$_{5000}$ (x).
Figure 4D:
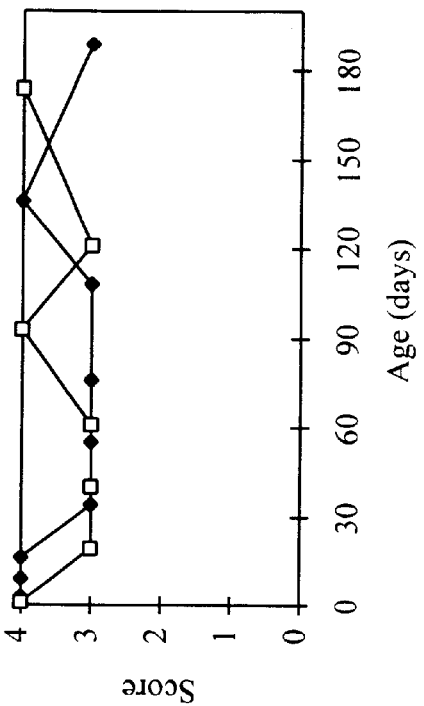
Figure 4A:
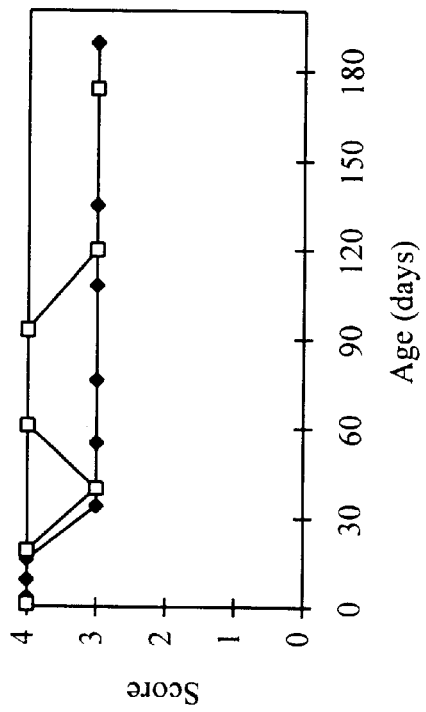
Figure 4B:
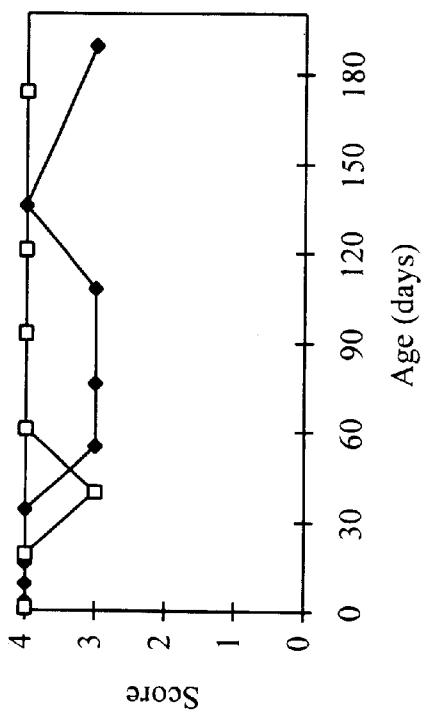
Figure 4E:
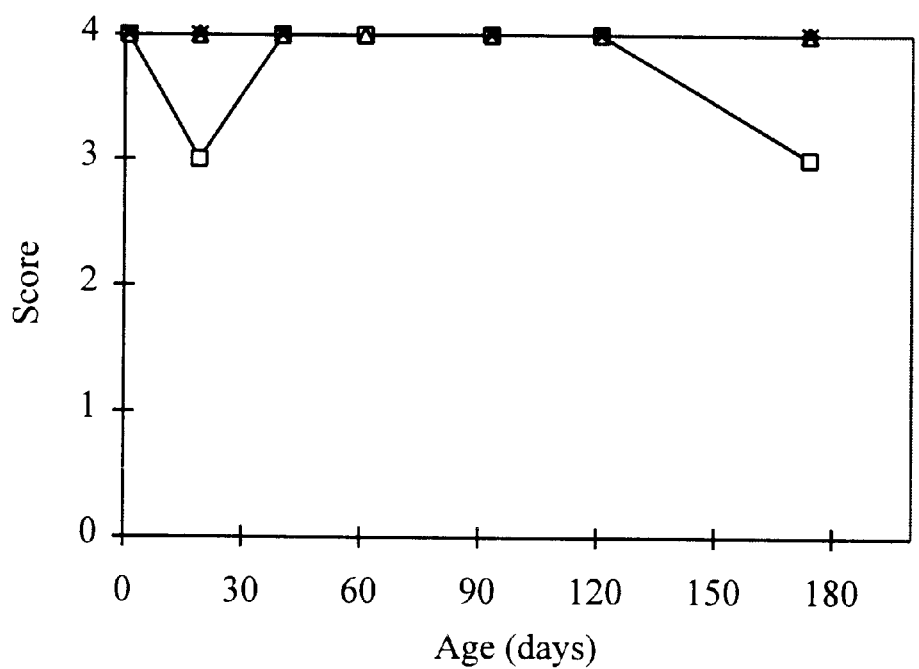

Accordingly, turbidity measurements of particulate suspensions in media of varying osmotic strength can be indicative of whether or not a particle has entrapped aqueous volume. Thus a 0.1 ml sample containing 3.45 mg of DOPC:DOPE-PEG$_{2000}$:BrC16-paclitaxel (1:1:8 molar ratio) particles, prepared by the ethanol injection method (as set forth in Example 1 hereinabove), was diluted into 3 ml of each of the following solutions (final paclitaxel concentration: 0.66 mg/ml): H$_2$O, 75, 150 and 300 mM NaCl. Samples were monitored ($\lambda$=800 nm) over time for their turbidity using a UV-2101PC UV scanning spectrophotometer (Shimadzu Scientific Instruments, Inc). Results are presented in FIG. 2. No changes in absorbance was noted, indicating that the particles, unlike liposomes, are not osmotically active.

Example 5

Particle Size Analysis

Particles were prepared by the ethanol injection procedure (as set forth in Example 1 hereinabove) with DSPE-PEG$_{2000}$ and BrC16-paclitaxel (15:85 molar ratio); particle samples (~1–3 microliters) were subjected to size measurement by a Submicron Particle Sizer (model 370), from NICOMP Particle Sizing Systems, Inc; the "solid particle" mode was used throughout. Mean particle diameters (nm) in suspensions of particles of various composition, as measured by number, intensity or volume weighting, are presented in Table 2 below.

TABLE 2

Nicomp Particle Size Analysis (nm)

| Lipid | Particle Weighted By | | |
|---|---|---|---|
| | Number | Intensity | Volume |
| DOPE-PEG$_{2000}$ | 20–119 | 96–208 | 44–181 |
| DSPE-PEG$_{2000}$ | 32–81 | 94–197 | 57–147 |
| DPPE-PEG$_{2000}$ | 43–93 | 104–172 | 69–138 |
| DMPE-PEG$_{2000}$ | 54 | 111 | 80 |
| DOPE-PEG$_{5000}$ | 34 | 68 | 48 |
| DSPE-PEG$_{5000}$ | 35 | 69 | 49 |
| DPPE-PEG$_{5000}$ | 34 | 73 | 50 |
| DMPE-PEG$_{5000}$ | 15–36 | 85–137 | 31–56 |

Example 6

Storage

Particles prepared in accordance with the ethanol injection procedure (as set forth in Example 1 hereinabove) so as to contain an 85:15 molar ratio of BrC16-paclitaxel and either DOPE-PEG$_{2000}$, DPPE-PEG$_{2000}$, DMPE-PEG$_{2000}$, DOPE-PEG$_{5000}$, DSPE-PEG$_{5000}$, DPPE-PEG$_{5000}$ or DMPE-PEG$_{5000}$ were suspended in the HEPES buffer and stored undiluted. A 20:80 molar ratio sample of BrC16-paclitaxel and DSPE-PEG$_{2000}$ was prepared by the REV process set forth in Example 1 hereinabove. Samples were stored, either at room temperature or at 4° C., and subsequently observed under a light microscope (Olympus BH-2, New York/New Jersey Scientific). The observed samples were scored subjectively for the presence of particles and crystallization of the hydrophobic compound; results are presented in FIGS. 3 and 4.

Figure 5:
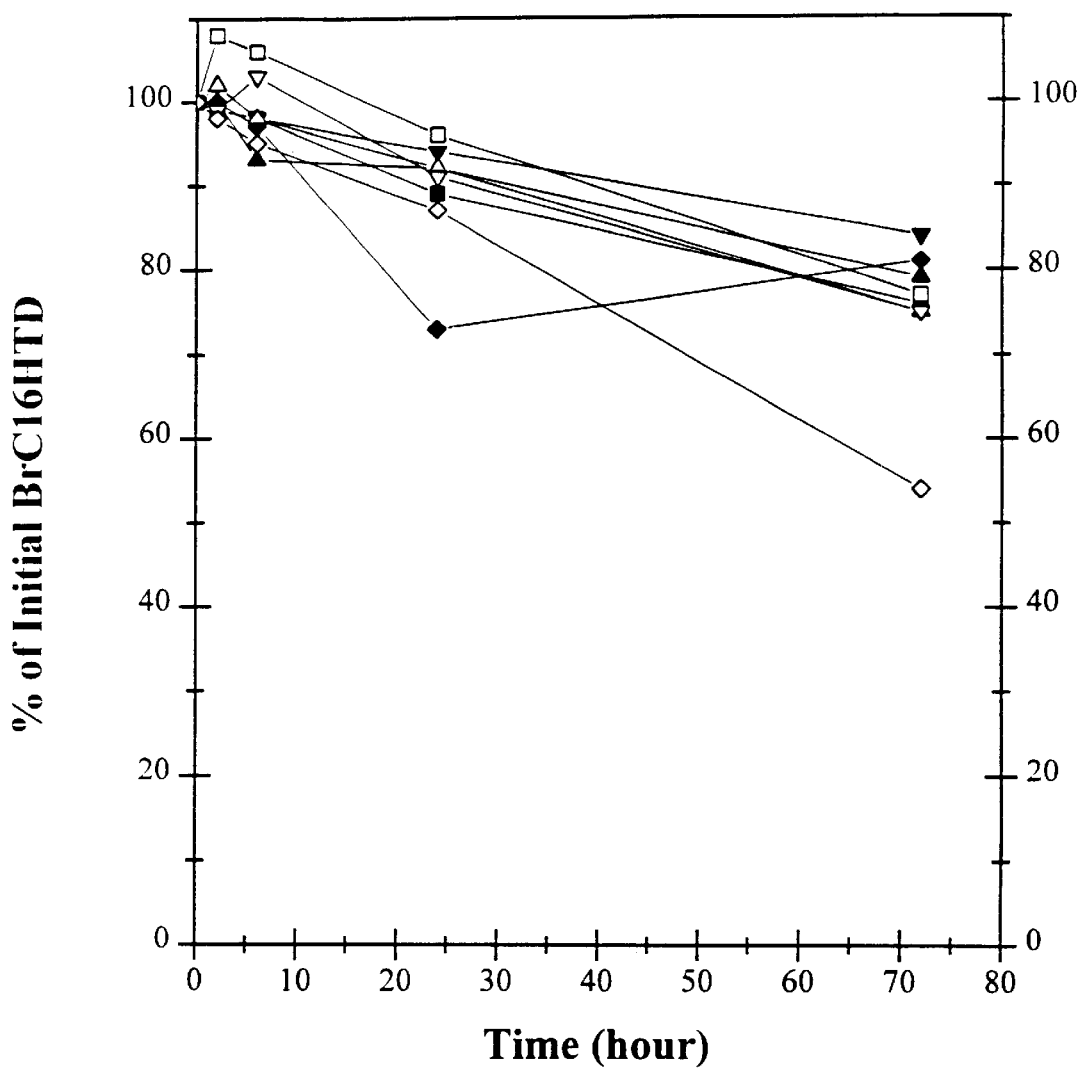
FIG. 5. Stability of Preparations Incubated in Rat Plasma. X-axis: time (hours). Y-axis: percent of bromylated paclitaxel remaining. PE-PEG formulations (each at a 15:85 molar ratio) - ■: DSPE-PEG$_{2000}$; ▲: DPPE-PEG$_{2000}$; ▼: DMPE-PEG$_{2000}$; ♦: DOPE-PEG$_{2000}$; ◇: DOPE-PEG$_{5000}$; □: DSPE-PEG$_{5000}$; Δ: DPPE-PEG$_{5000}$; ∇: DMPE-PEG$_{5000}$.

Particles suspended in the HEPES buffer were also added to fresh male rat plasma (Fisher Rat, Strain: f344, age: ~60 days, weight: 175–200 gram, inbreded, final derivatized compound concentration: 0.2 mg/ml); the plasma samples were incubated at 37° C. for 0, 2, 6, 24 or 72 hours. Immediately after the incubation, the samples were frozen by liquid nitrogen and stored at −70° C., then thawed to room temperature and added to an equal volume of acetonitrile containing 0.04 mg/ml(final) C12-paclitaxel as an internal standard. The mixtures were centrifuged at 1000 rpm for 10 minutes using a Eppendorf Centrifuge 5402, and then analyzed for concentrations of BrC16-paclitaxel by HPLC. Results are presented in FIG. 5.

BrC16-paclitaxel/DSPE-PEG$_{2000}$ (85:15) particle samples were also subjected to particle size analysis (as set forth in Example 5, hereinabove) after an extended period of storage at 4 degrees Celsius; results are presented in Table 3. Each sample was prepared separately. The results indicate the initial size determination and the size determination after the storage period. Clearly particle size was maintained for extended periods of time at 4° C.

TABLE 3

| | Nicomp Particle Size Analysis (nm) Particle Size (Initial/Final) as Weighted By | | |
|---|---|---|---|
| # of Days in Storage | Number | Intensity | Volume |
| 21 | 56/59 | 140/142 | 94/98 |
| 31 | 53/61 | 143/145 | 94/101 |
| 59 | 48/60 | 135/135 | 86/95 |
| 100 | 48/52 | 138/139 | 87/91 |
| 114 | 46/45 | 144/150 | 89/90 |
| 141 | 43/35 | 116/117 | 73/67 |

Example 7

Light Microscopy

Figure 6A:
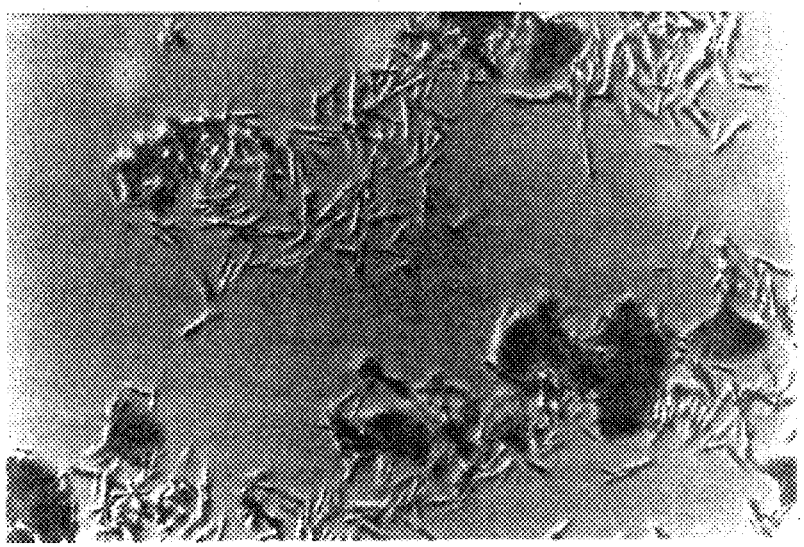
FIGS. 6A–6H. Light Microscopy Photographs of Various Paclitaxel-Containing Preparations. A: DSPE-PEG$_{2000}$:Paclitaxel (80:20 molar ratio); B: DSPE-PEG$_{2000}$:Paclitaxel (80:20); C: DOPE-PEG$_{2000}$:BrC8-Paclitaxel (20:80); D: DOPE-PEG$_{2000}$:BrC6-Paclitaxel (20:80); E: DOPE-PEG$_{2000}$:BrC14-Paclitaxel (20:80); F: DOPE-PEG$_{2000}$:BrC12-Paclitaxel (20:80); G: DSPE-PEG$_{2000}$:BrC16-Paclitaxel (10:90); H: DOPE-PEG$_{2000}$:BrC16-Paclitaxel (20:80).
Figure 6B:
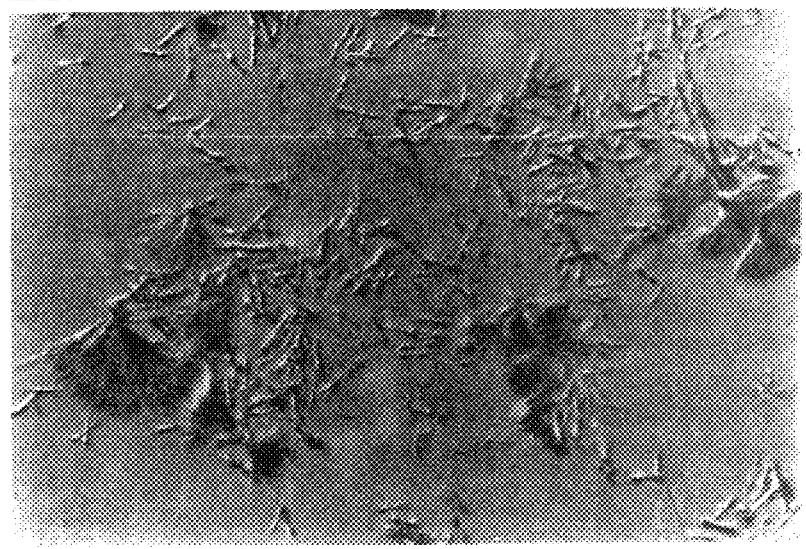
Figure 6C:
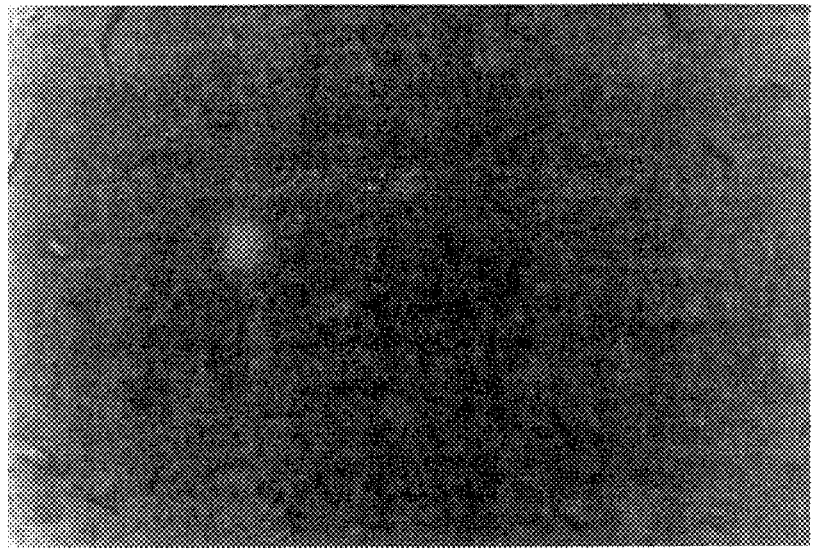
Figure 6D:
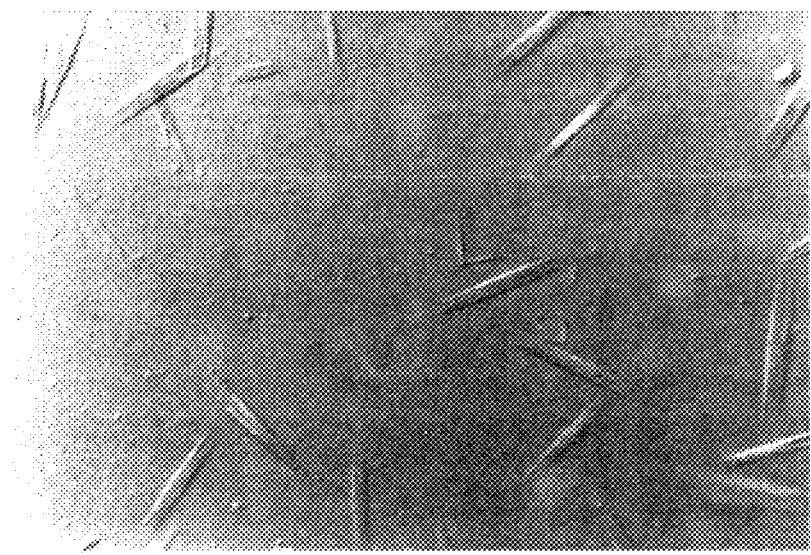
Figure 6E:
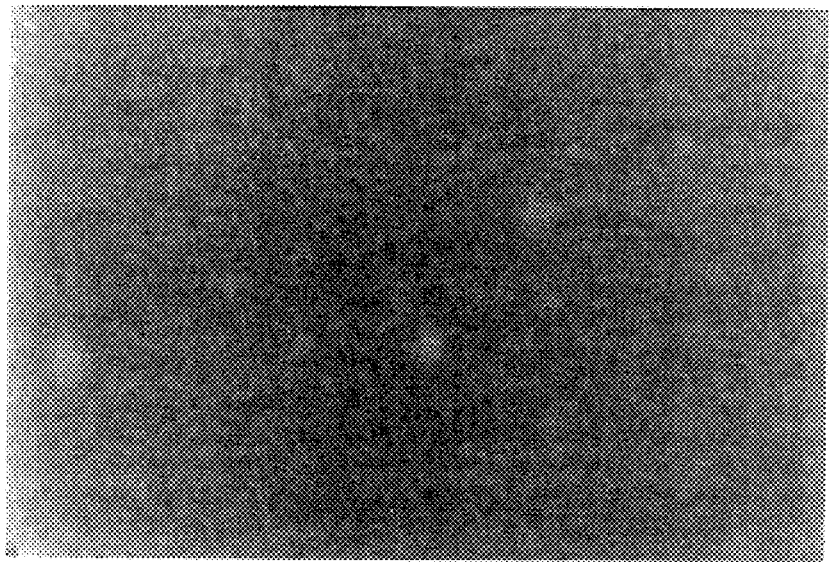
Figure 6F:
Figure 6G:
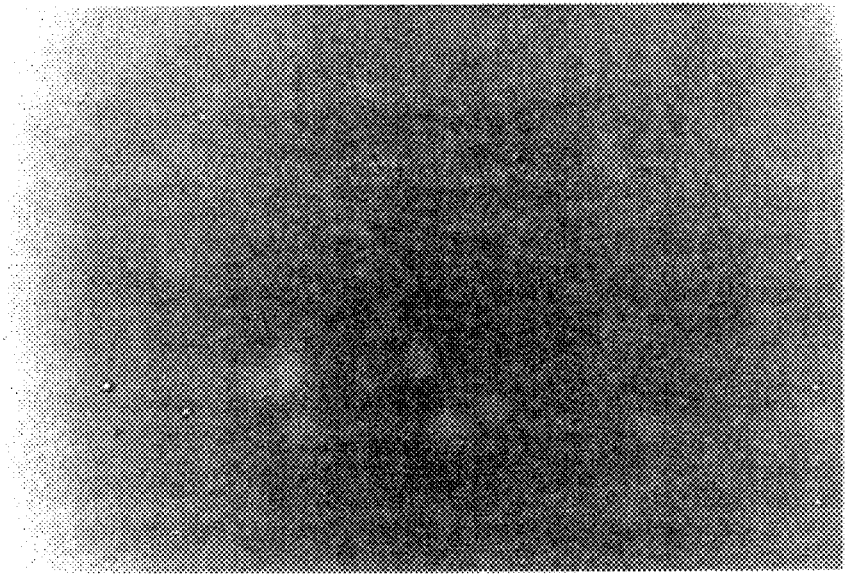
Figure 6H:
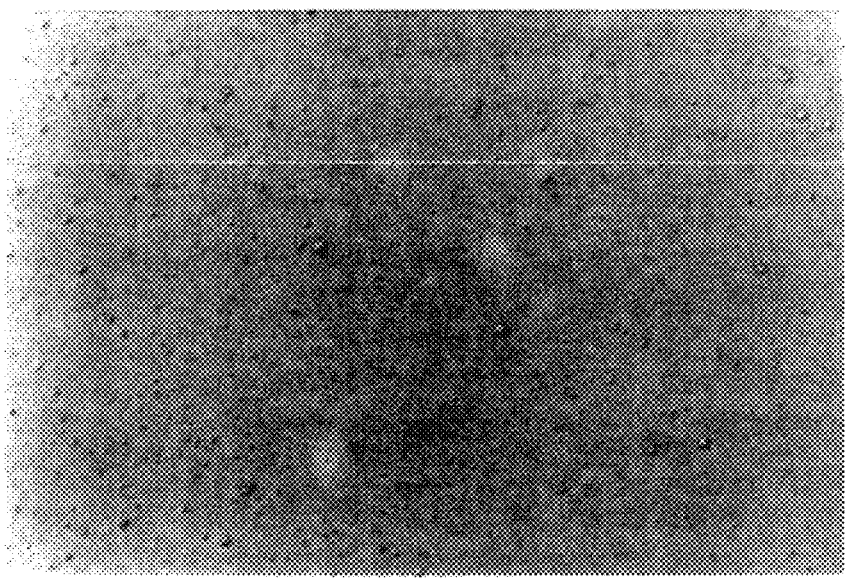

DSPE-PEG$_{2000}$ and paclitaxel (80:20, molar ratio) were combined according to the reverse-phase evaporation process (as set forth in Example 1 hereinabove); the paclitaxel was not attached to a hydrophobic domain. Light micrographs (Olympus BH-2, New York/New Jersey Scientific) of these particles were taken at a magnification of 200× (see FIG. 6, final magnification 277× for FIGS. 6A and 6B). Crystals were observed to be the predominant structure.

DOPE-PEG$_{2000}$:Br-paclitaxel (80:20) particles, wherein the acyl chain covalently attached to paclitaxel was of a varying length, were prepared by the ethanol injection process (as set forth in Example 1 hereinabove); light micrographs of these particles (550×) are presented in FIGS. 6C–6H.

Vinblastine was covalently attached to an acyl chain at the 20-position hydroxyl group)by a modification of the method disclosed in U.S. Pat. Nos. 5,580,899 and 5,703,117 (incorporated herein by reference). Briefly, Vinblastine (25 mg) dissolved in $CH_2Cl_2$ and pyridine (5:1) was heated at reflux at 41° C. overnight with excess of palmitoyl chloride (60 μl) in presence of 4 mg of DMAP. Thin layer chromatography (TLC) in $CHCl_3$:MeOH (95:5), showed nearly all (>95%) of the starting material had reacted to yield a C16-product. Solvents were evaporated under reduced pressure and the product was purified by preparative TLC using $CHCl_3$;MeOH (95:5). Finally, the product was lyophilized from cyclohexane to yield 15 mg (54%) of a white solid powder, which was characterized by $^1H$ and $^{13}C$ NMR.

Figure 8A:
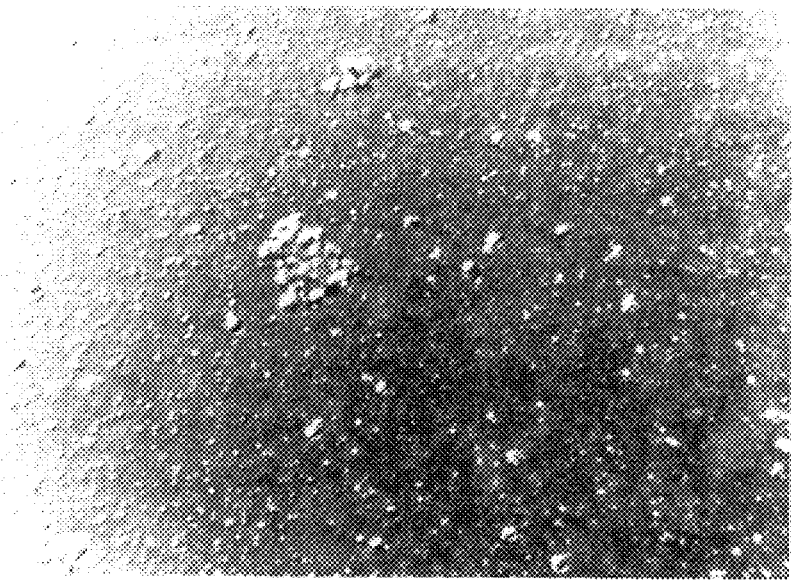
FIGS. 8A–8D. Micrographs of DSPE-PEG$_{2000}$:C16-Vinblastine (40:60 Molar Ratio) Preparations. A, B: Light microscopy; C, D: electron microscopy.
Figure 8B:
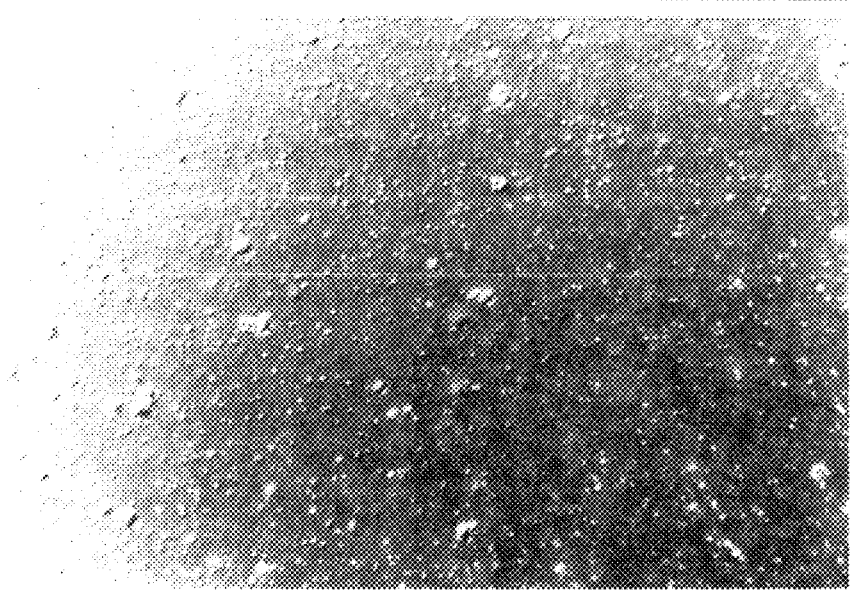

DSPE-PEG$_{2000}$:C16-vinblastine particles were prepared (40:60 molar ratio) by the REV process (as set forth in Example 1 hereinabove), using 18 mg of DSPE-PEG$_{2000}$ and 11 mg of C16-vinblastine, suspended in 1.1 ml of the HEPES buffer. Light micrographs (277×) of the resultant particles are presented in FIGS. 8A and 8B, hereinbelow.

Camptothecin was covalently attached to an acyl chain at the 20-position hydroxyl group) by a modification of the method disclosed in U.S. Pat. Nos. 5,580,899 and 5,703,117 (incorporated herein by reference). Briefly, Camptothecin (20 mg), dissolved at room temperature in 4 ml of anhydrous pyridine, was stirred with 56 mg palmitic anhydride for 48 hrs. Thin layer chromatography (TLC) in $CHCl_3$:MeOH (96:4) showed the progress of the reaction. Pyridine was evaporated under reduced pressure and the residue obtained was purified on a preparative TLC using $CHCl_3$:MeOH (96:4). 30.1 mg (90%) of the product was obtained as a cream colored flaky powder, which was characterized by $^1H$ and $^{13}C$ NMR.

DSPE-PEG$_{2000}$:C16-camptothecin (camptothecin conjugated, by way of its 20-position OH group, to a 16-carbon saturated acyl chain) particles having a 40:60 molar ratio were prepared by the REV process (as set forth in Example 1 hereinabove), using 50 mg of DSPE-PEG$_{2000}$ and 15 mg of C16-camptothecin suspended in 1.5 ml of the HEPES buffer.

Example 8

Freeze Fracture Electron Microscopy

Figure 7A:
FIGS. 7A–7B. Freeze-Fracture Electron Micrographs (A and B) of DOPC:DOPE-PEG$_{2000}$:BrC16-Paclitaxel (30:50:20 Molar Ratio) Preparations.
Figure 7B:
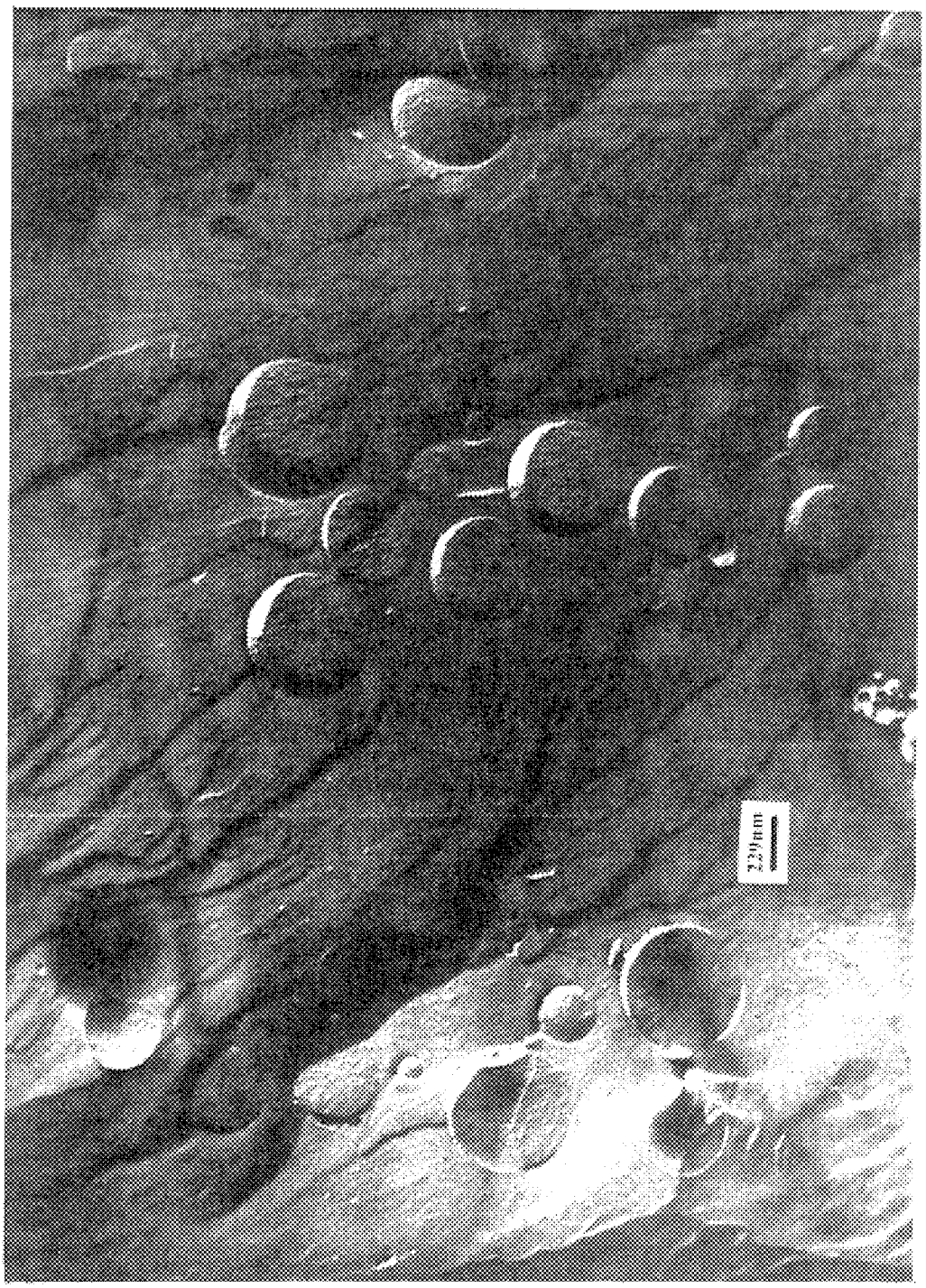

DOPC:DOPE-PEG$_{2000}$:BrC16-paclitaxel (30:50:20) particles were prepared by the REV process (as set forth in Example 1 hereinabove) using 4.7 mg of DOPC, 27.4 mg of DOPE-PEG$_{2000}$ and 5.85 mg of BrC16-paclitaxel, suspended in 1 ml of the HEPES buffer. Freeze fracture electron replicas, at magnifications of about 91,000× (see FIG. 7A) and about 31,000× (see FIG. 7B), were made by placing 1–3 μl of sample between a pair of Balzers copper double replicating holders, then freezing from room temperature in liquid propane. The frozen samples were fractured (at −100° C. and $10^{-6}$–$10^{-7}$ mbar), and shadowed with platinum (∠45°) and carbon in a Balzers BAF400 freeze-fracture device. Replicas were cleaned overnight in 5% hypochlorite (commercial bleach), washed in distilled water, mounted on 300 mesh grids and viewed with a Philips 300 TEM. The image indicated that particles have a solid interior with no observable lamella.

Figure 8C:
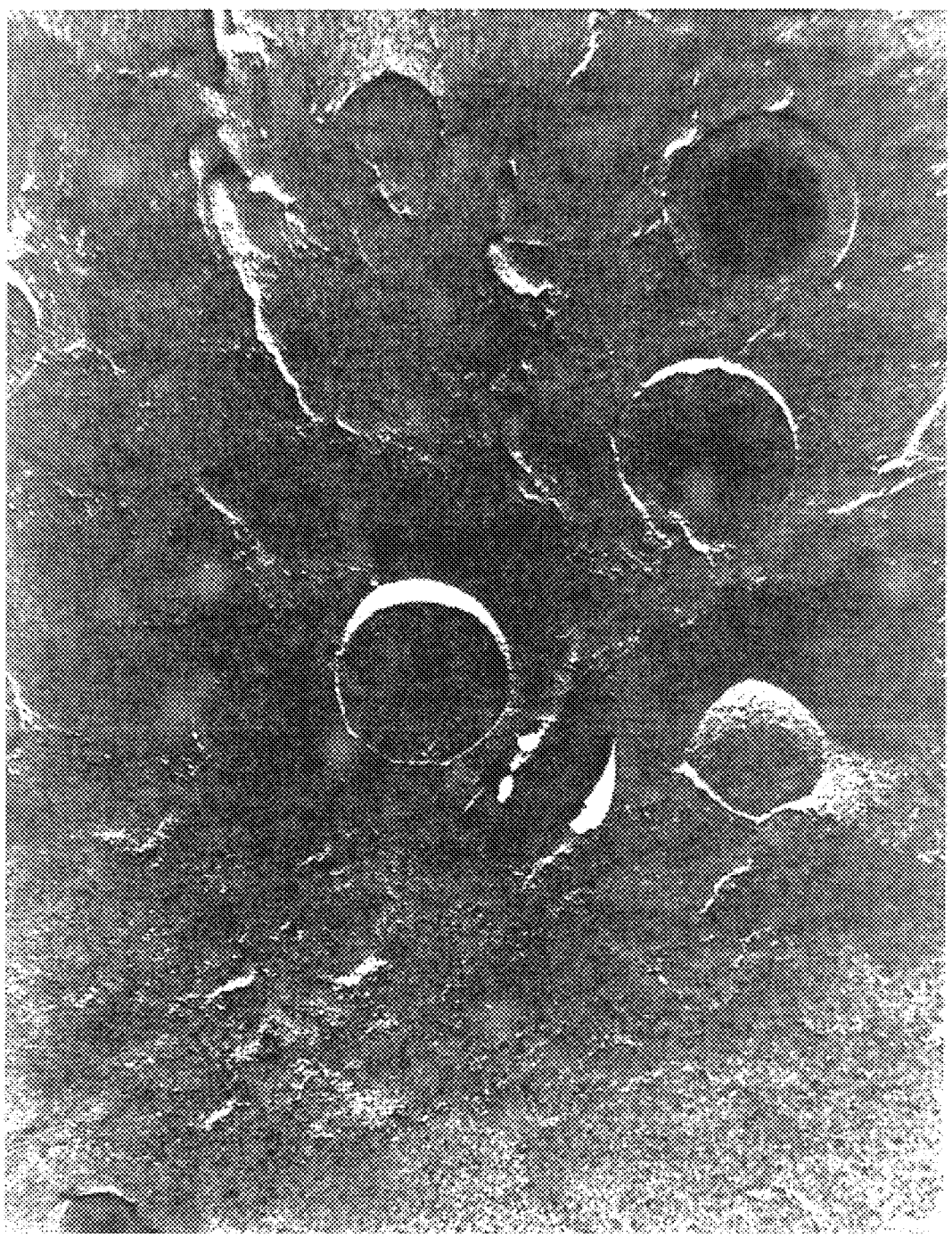
Figure 8D:
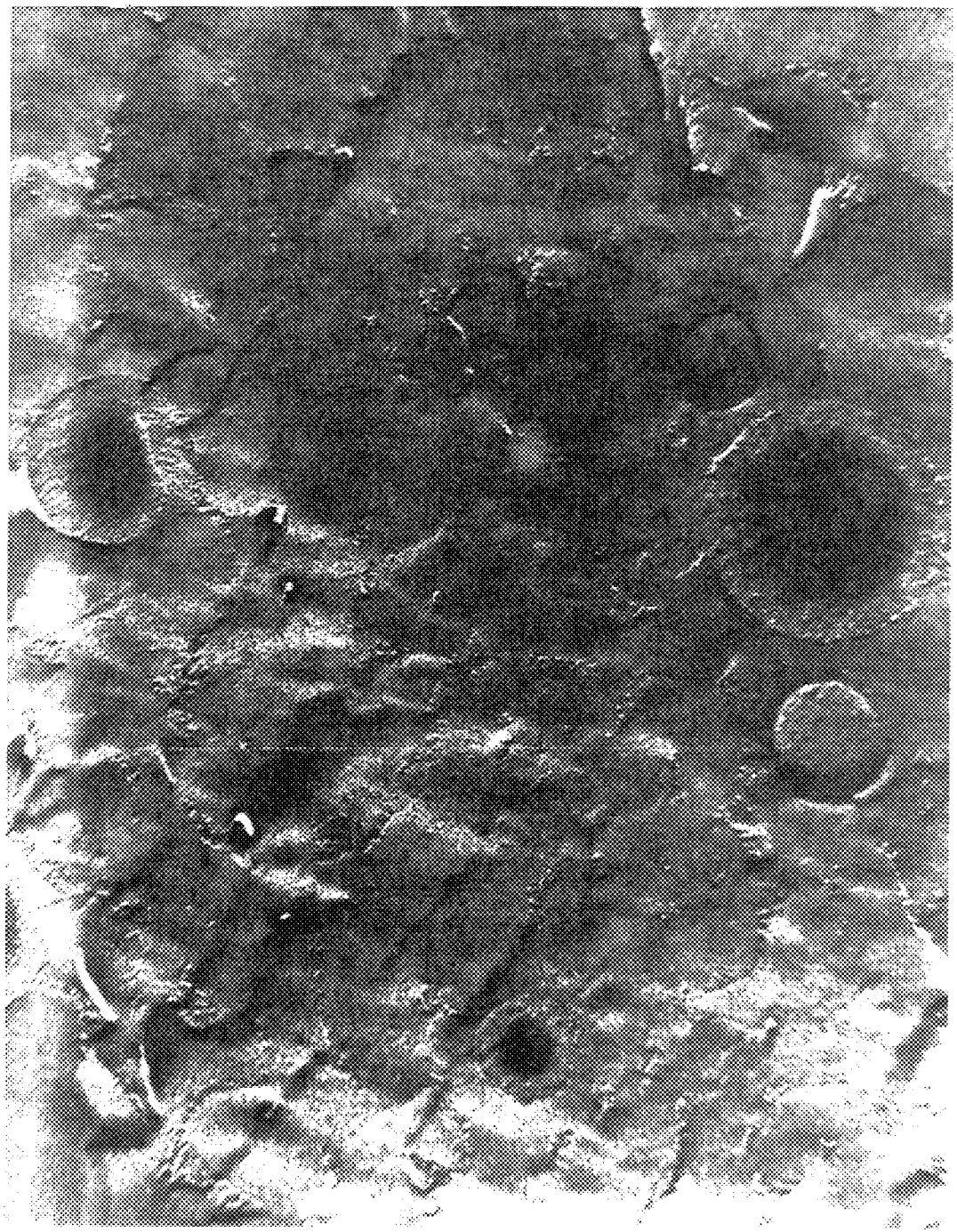
Figure 9A:
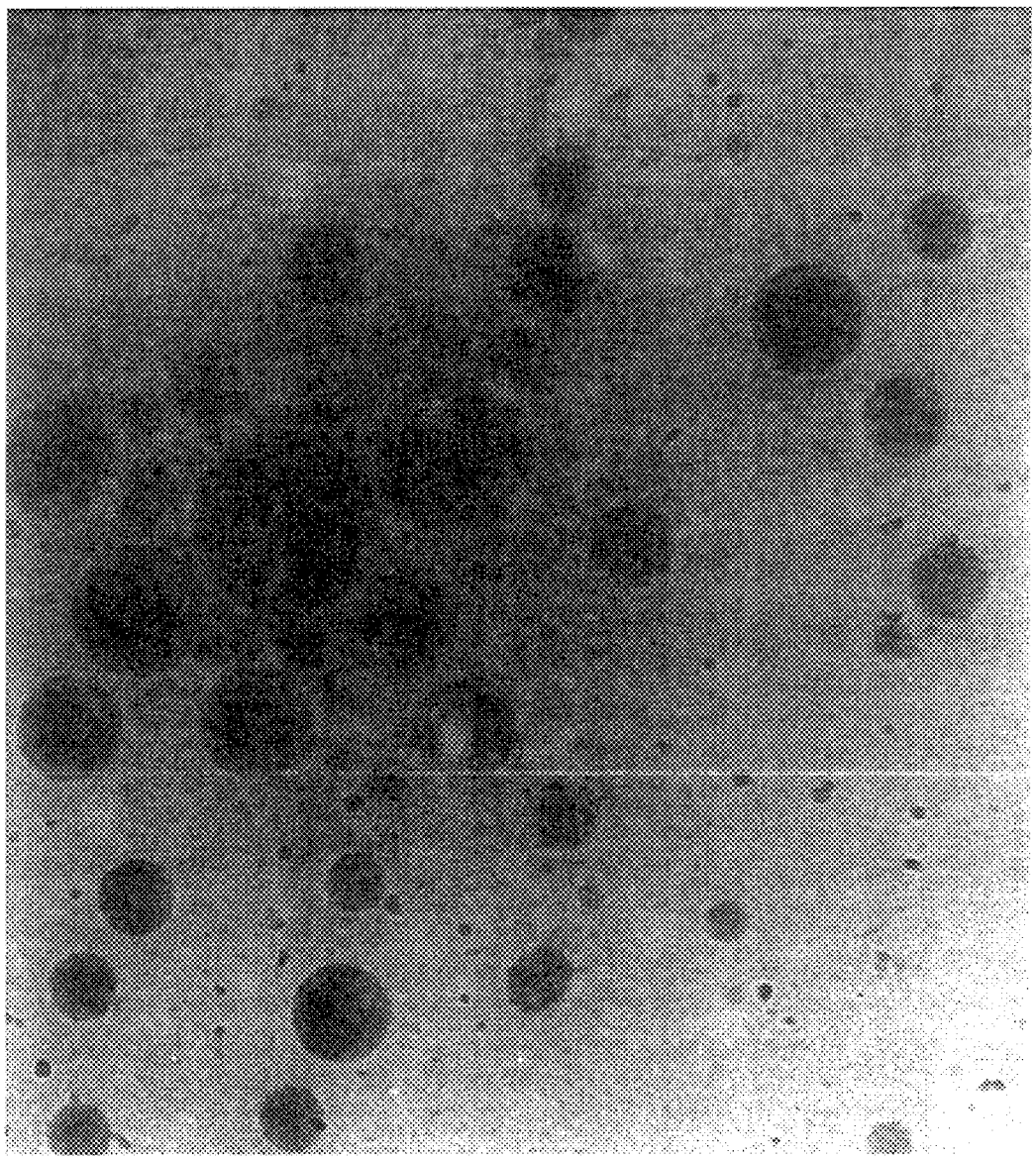
FIGS. 9A–9D. Cryo-electron Micrographs (A–D) of Particles Composed of DSPE-PEG$_{2000}$ and BrC16-paclitaxel (15:85 Molar Ratio).
Figure 9B:
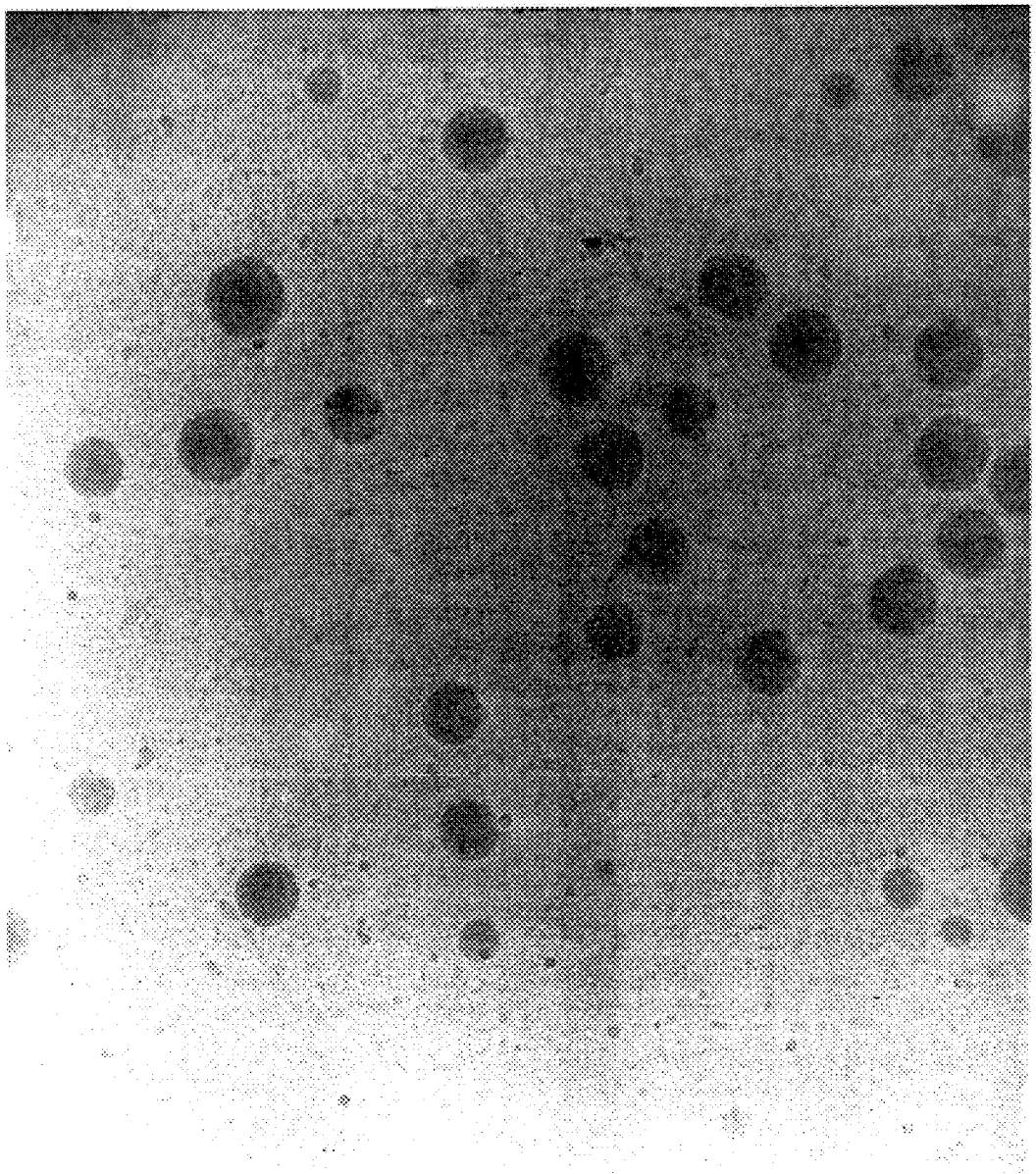
Figure 9C:
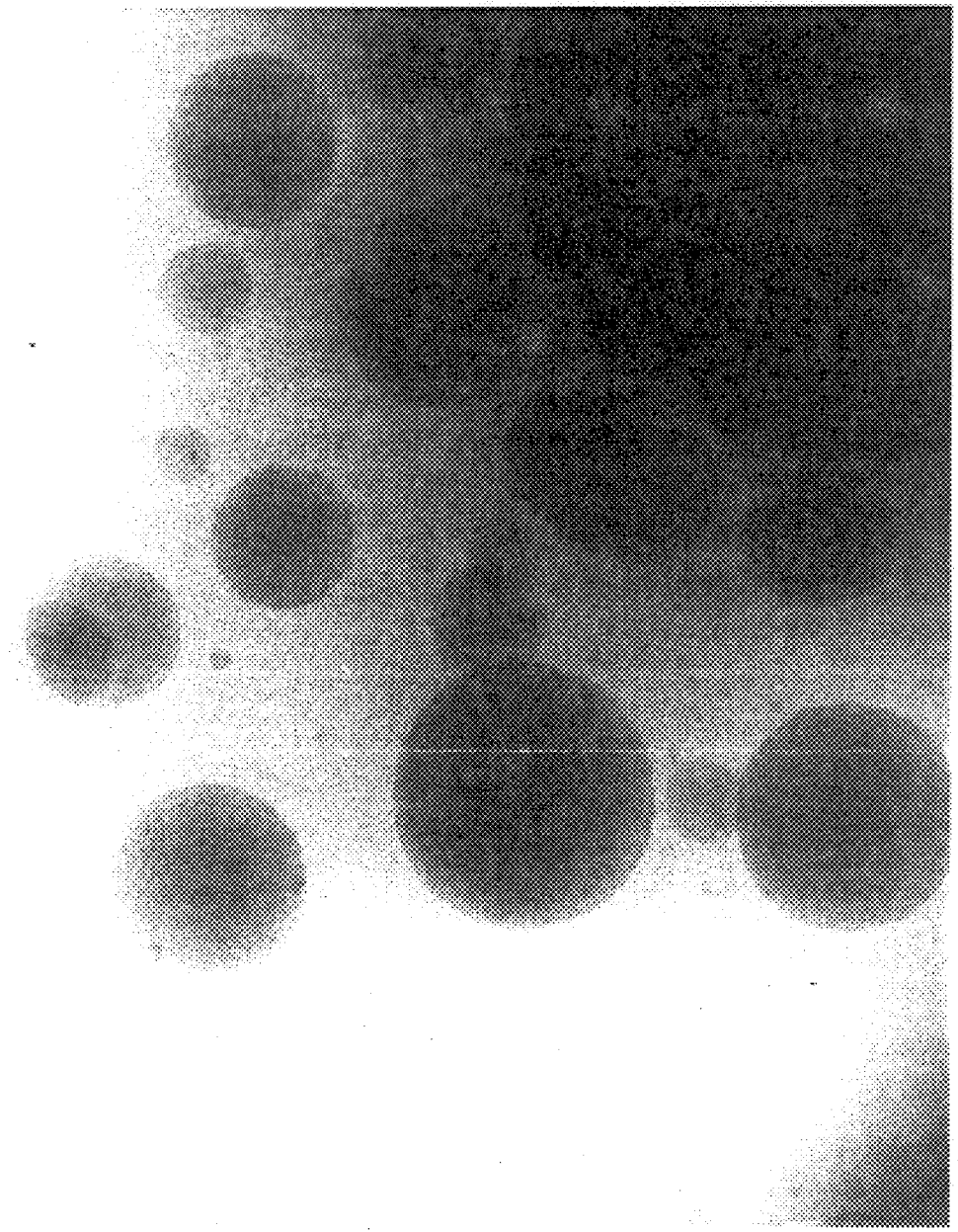
Figure 9D:
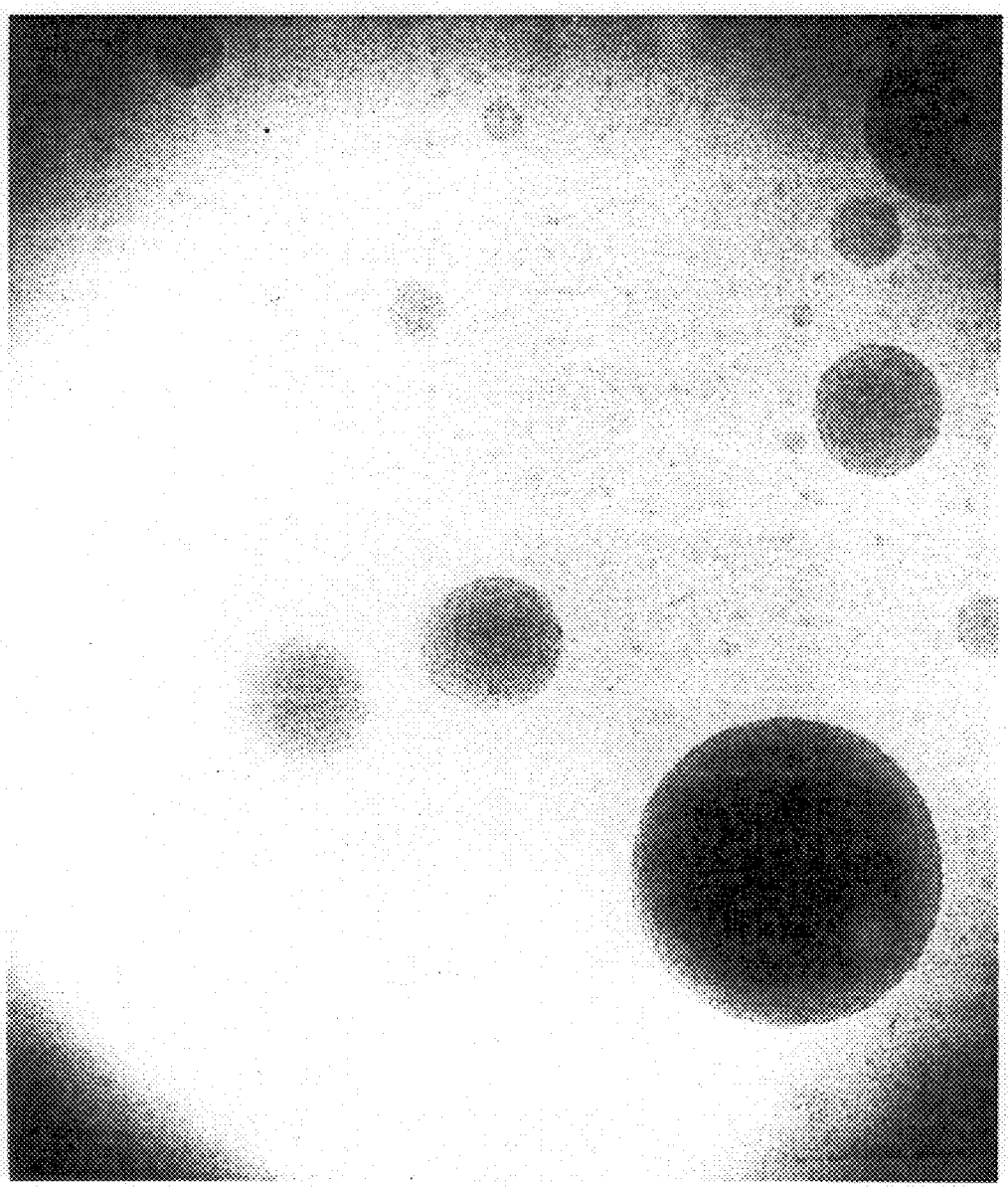

DSPE-PEG$_{2000}$:C16-vinblastine (40:60 molar ratio) particles were prepared by the REV process (as set forth in Example 1 hereinabove) using 18 mg of DSPE-PEG$_{2000}$ and 11 mg of C16-vinblastine suspended in 1.1 ml of the HEPES buffer. The resulting particles were processed for electron microscopy by the procedures set forth above; electron micrographs (55,000×) are presented in FIGS. 8C and 8D. The image obtained by cryo-EM again indicated that these particles have a solid core with no internal lamella.

Example 9

Cryo-Electron Microscopy

Particles were prepared according to the ethanol injection procedure (as set forth in Example 1, hereinabove) with DSPE-PEG$_{2000}$ and BrC16-paclitaxel (15:85) so as to contain about 10 mg/ml BrC16-paclitaxel; samples (1 ml volume) were kept at room temperature while grids were prepared. Undiluted samples were frozen by a process involving the steps of placing a drop of sample on an EM grid, blotting the drop to a thin film, and then plunging the blotted grid into liquid ethane. Photographic negatives were taken of frozen hydrated samples suspended in holes in a lacy carbon support, under low electron dose conditions. The lens was focused 1.8 μm for 60 K, and 1.5 μm for 100 K. Results are presented in FIG. 9 (magnification 110,000× for figures A and B, 184,000× for figures C and D).

Example 10

Captured Volume Measurements

Particles were prepared as set forth in example 1 hereinabove, so as to achieve a suspension of particles in which the concentration of BrC16HTD was 10 mg/ml and the concentration of DSPE-PEG$_{2000}$ was 4 mg/ml. Liposome suspensions were also prepared according to the ethanol injection method, with DSPC, so as to have a lipid concentration of 14 mg/ml. Captured volumes of these particles and liposomes (see Table 4, hereinbelow) were measured according to the methods of Perkins et al. (Chemistry and Physics of Lipids, 64 (19930 197–217; the contents of which are incorporated herein by reference) using the spin label probe tempone, introduced into the preparations either in ethanol (method #1) or in the HEPES buffer (method #2).

For concentrating particles by centrifugation, following cooling to room temperature, particles were collected by centrifugation of suspension samples (1.5 ml) at 50,000 g, using a Beckman L5-50 model ultracentrifuge. The pellet was resuspended in about 0.4 ml of the same buffer. The Tempone-containing samples were divided into two 100-microliter aliquots, to one of which was added HEPES buffer, the other aliquot receiving 100 microliters of a 100 mM solution of the broadening agent ("BA") chromium oxalate.

ESR (electron spin resonance; i=−1 resonance) without broadening agent is related to total aqueous volume by the equation: $A_{tot}=V_{in}+V_{out}=V_{tot}-V_{lipid}$ ($V_{in}$=internal volume; $V_{tot}$=suspension volume; and, $V_{lipid}$=hydrated lipid volume (calculated from the specific volumes of the lipids and the internal lipid concentration subsequent to dilution)). Internal volume was then calculated as the product of (1) the signal amplitude ($A_{BA}$) of an aliquot of sample mixed together with the broadening agent, and (2) a correction factor for the lipid volume, according to the equation: $V_{in}=A_{BA}\times[(V_{tot}-V_{lipid})/A_{tot}]$. Both measurements ($A_{tot}$ and $A_{BA}$) used samples diluted to the same concentration. Captured volume was calculated using the internal volume ($V_{in}$, microliters) and the lipid concentration (micromoles/ml).

TABLE 4

|  | Liposomes | | Particles | | Particles (pellet) | |
| --- | --- | --- | --- | --- | --- | --- |
|  | Method 1 | Method 2 | Method 1 | Method 2 | Method 1 | Method 2 |
| Relative signal amplitude (w/ BA) | 62 | 51 | 62 | 54 | 63 | 59 |
| Relative signal amplitude (w/o BA) | 13 | 12 | 0 | 0 | 0 | 0 |
| Captured volume (microliters/ micromole lipid) | 2.7 | 3.0 | 0 | 0 | 0 | 0 |

Example 11

Acute Toxicity Studies

DSPE-PEG$_{2000}$/BrC16-paclitaxel containing particles, prepared as described hereinabove and Taxol® (Bristol Myers-Squibb) were administered either intraperitoneally (i.p.) or intravenously (i.v.) to groups of 5–10 CDF1 female mice, in five daily doses ranging from 12.5 to 400 mg/kg of either BrC16-paclitaxel in the particles or paclitaxel in Taxol® (at such equal mg/kg doses, the molar doses of the BrC16-paclitaxel were 27% lower than the molar doses of paclitaxel in Taxol®; molecular weight BrC16-paclitaxel: 1169; molecular weight paclitaxel: 853).

Stock formulations were diluted in phosphate-buffered saline (PBS) to the desired concentrations, and administered at a dose volume of 25 ml/kg; PBS was used as the control. Mice were checked daily, and the survival time of each member in each group was determined. Results of the acute toxicity following intraperitoneal (i.p.) and intravenous (i.v.) administration are presented in Tables 5 and 6, respectively. These results represent pooled data from 1–4 experiments for each formulation and at each dose level.

TABLE 5

Acute Toxicity of BrC16-Paclitaxel vs. Taxol ® in CDF1 Mice (i.p. × 5)

| Daily Dose | Paclitaxel Equivalent | # Mice Surviving/Total | |
| --- | --- | --- | --- |
| (mg/kg) | (mg/kg) | BrC16-Paclitaxel | Taxol ® |
| 12.5 | — | — | 20/20 |
| 25 | — | — | 10/20 |
| 37.5 | — | — | 0/10 |
| 50 | — | — | 0/25 |
| 100 | 72 | 6/6 | — |
| 200 | 144 | 10/11 | — |
| 300 | 216 | 5/6 | — |
| 400 | 288 | 1/6 | — |

* Survival at 30 days post-injection.

TABLE 6

Acute Toxicity of BrC16-Paclitaxel vs. Taxol ® in CDF1 Mice (i.v. × 5)

| Daily Dose | Paclitaxel Equivalent | # Mice Surviving/Total * | |
| --- | --- | --- | --- |
| (mg/kg) | (mg/kg) | BrC16-Paclitaxel | Taxol ® |
| 12.5 | — | — | 15/15 |
| 18.75 | — | — | 5/5 |
| 25 | — | — | 13/15 |
| 31.25 | — | — | 4/5 |
| 37.5 | — | — | 0/7 |
| 50 | 36 | 5/5 | 0/8 |
| 100 | 72 | 4/5 | — |

* Survival at 30 days post-injection.

Example 12

Anticancer Therapeutic Studies

Figure 10:
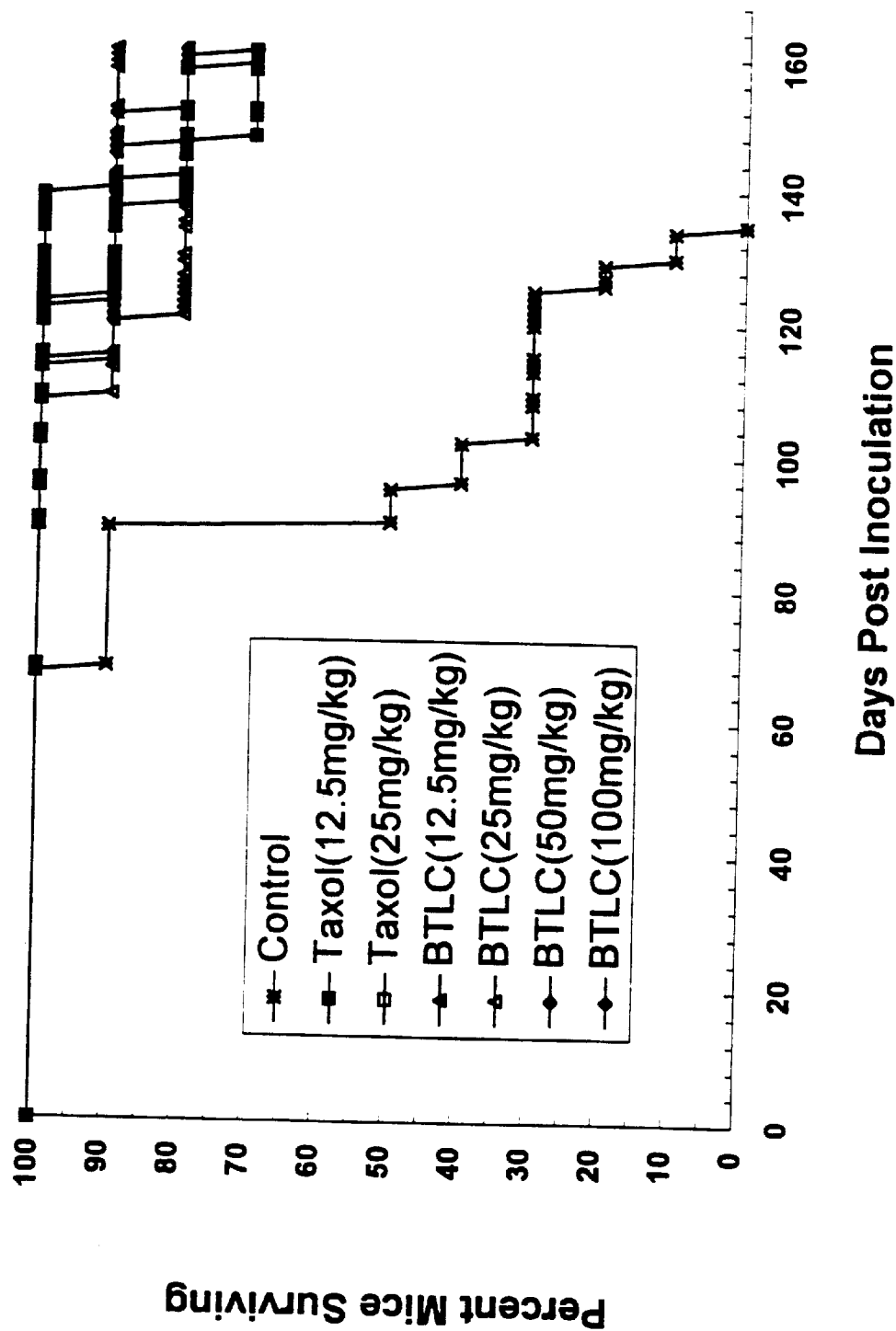
FIG. 10. Effects of DSPE-PEG$_{2000}$:BrC16-paclitaxel (15:85)-Containing Particles vs. Taxol® on Established Ovcar3 Tumors in SCID Mice. Treatment, intraperitoneally, at days 20, 22, 24, 26 and 28 post-inoculation with: control (*); Taxol®, 12.5 mg paclitaxel/kg (■); Taxol, 25 mg paclitaxel/kg (□); BrC16-paclitaxel, 12.5 mg/kg (▲); 25 mg BrC16-paclitaxel /kg (Δ); BrC16-paclitaxel, 50 mg/kg (◇); BrC16-paclitaxel, 100 mg/kg (♦). X-axis: number of days post-inoculation; y-axis: percent survival.

Six-week old CB17 female SCID mice were inoculated (i.p.) with $5 \times 10^6$ Ovcar3 (human ovarian carcinoma) cells (day 0); BrC16-paclitaxel (12.5, 25, 50 or 100 mg/kg) or Taxol® (12.5 or 25 mg/kg) were then administered (i.p.) to the mice (10 mice/group) on days 20, 22, 24, 26 and 28 after tumor inoculation. Stock drug formulations were diluted in PBS to reach the desired dosage level; the diluted formulations were administered at a dose volume of 25 ml/kg. PBS was also used as a control. Mice were checked daily, and survival time for each member of each group was determined. Results are presented in FIG. 10.

Example 13

Anticancer Therapeutic Studies

Figure 11:
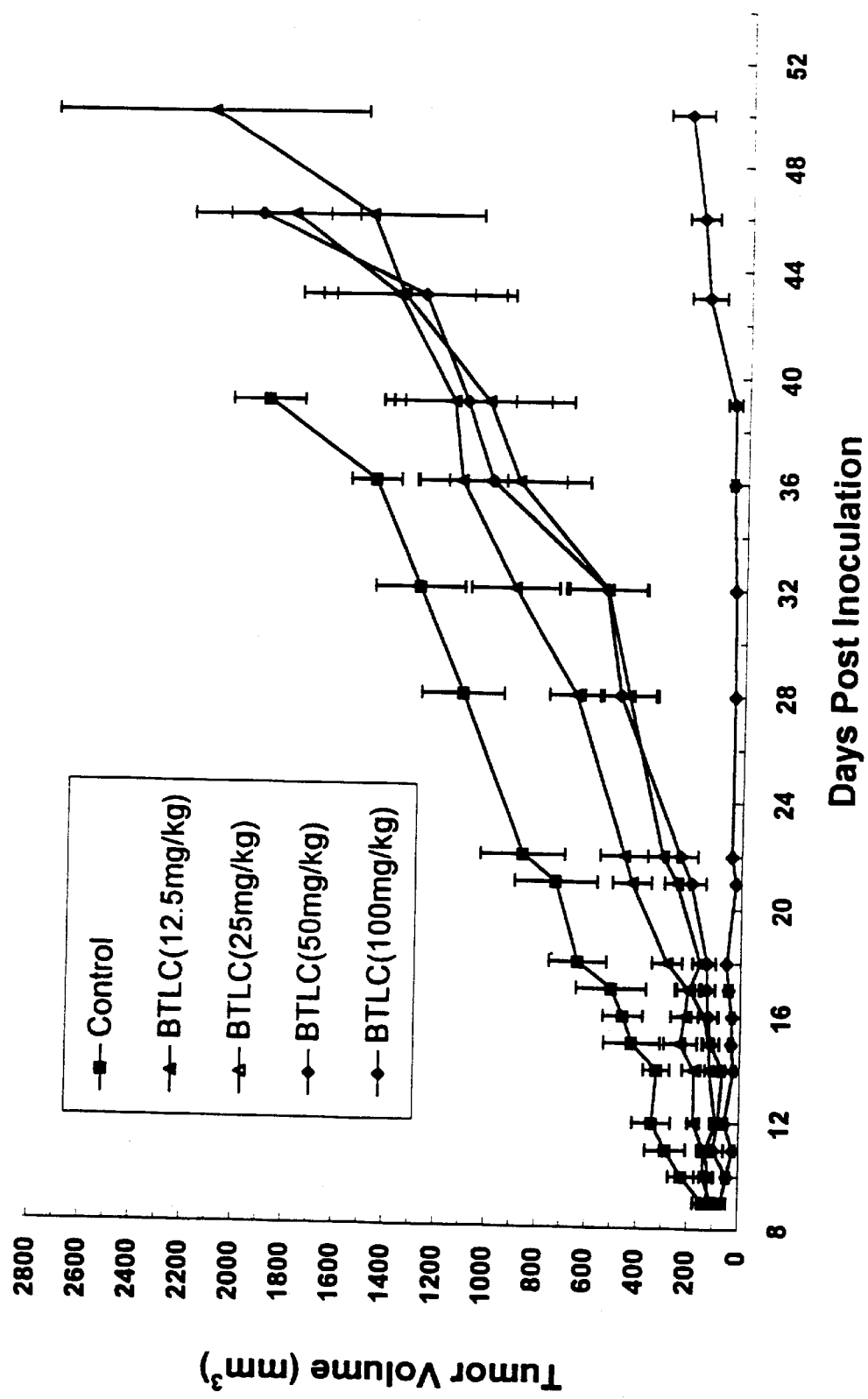
FIG. 11. Effect of DSPE-PEG$_{2000}$:BrC16-paclitaxel (15:85)-Containing Particles on A549 Human Non-Small Cell lung Carcinoma Lung Tumors Established in SCID Mice. Treatment, intravenously, at 1, 3, 5, 7 and 9 days post-inoculation with: control (■); BrC16-paclitaxel, 12.5 mg/kg (▲); 25 mg BrC16-paclitaxel /kg (Δ); BrC16-paclitaxel, 50 mg/kg (◇); BrC16-paclitaxel, 100 mg/kg (♦). X-axis: number of days post-inoculation; y-axis: tumor volume (mm$^3$).

Six-week old CB17 female SCID mice were inoculated (subcutaneously) with $5 \times 10^6$ A549 (human non-small cell lung carcinoma) cells (day 0); BrC16-paclitaxel (12.5, 25, 50 or 100 mg/kg) was then administered (i.v.) to the mice (5 mice/group) on days 1, 3, 5, 7 and 9 after tumor inoculation. Stock drug formulations were diluted in PBS to reach the desired dosage level; the diluted formulations were administered at a dose volume of 10 ml/kg. PBS was also used as a control. Tumor volumes ($mm^3$), calculated as $(width/2)^2 \times length \times \pi$, were measured twice weekly beginning on the ninth day post inoculation. Mice were sacrificed when their tumor volumes reached 1500 $mm^3$. Results are presented in FIG. 11.

Example 14

Anticancer Therapeutic Studies

Figure 12:
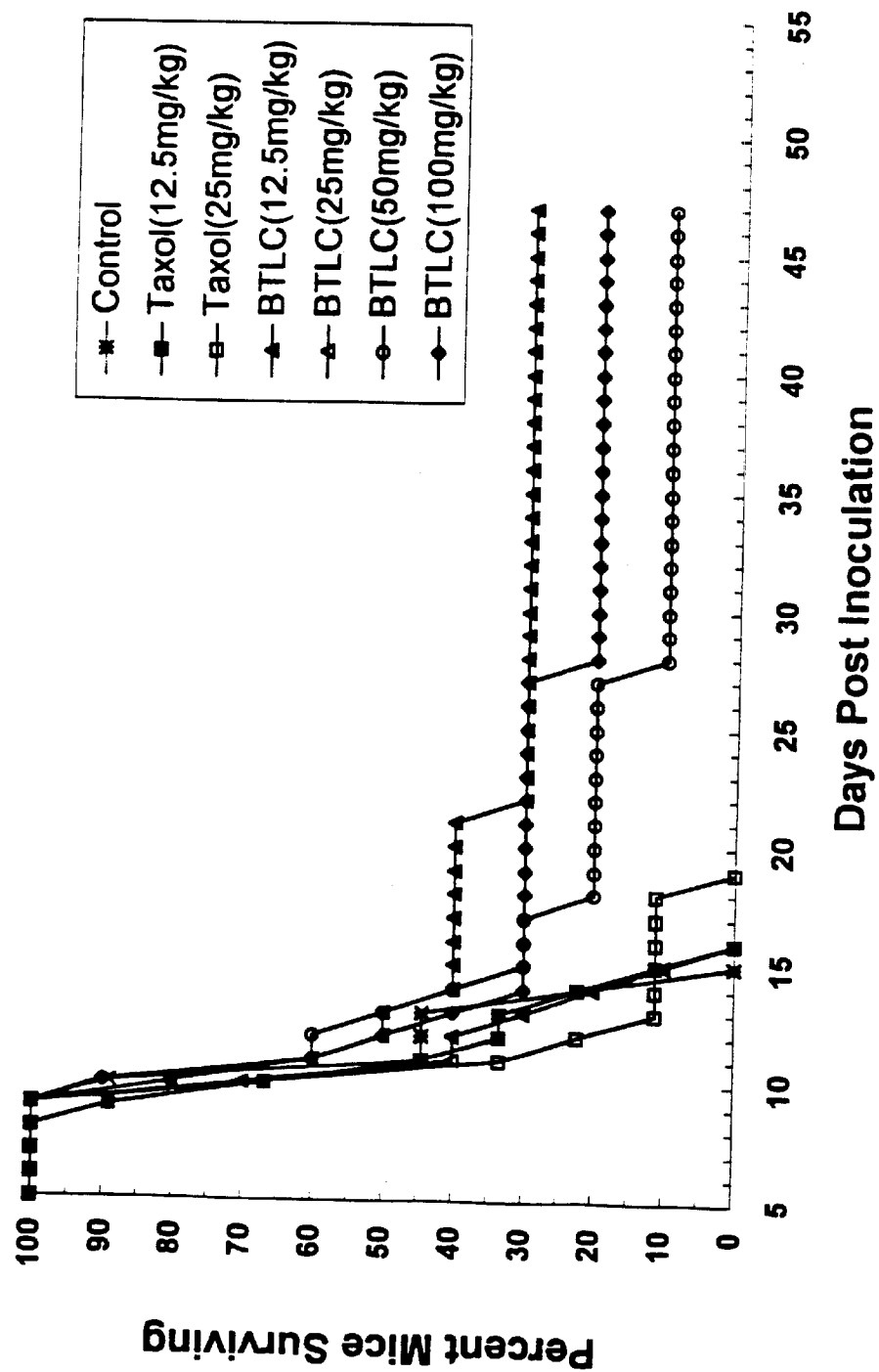
FIG. 12. Effects of DSPE-PEG$_{2000}$:BrC16-paclitaxel (15:85) vs. Taxol® on L1210 Murine Leukemias in CDF1 Mice. Treatment, orally and at 1–5 days post inoculation with L1210 cells, with: control (*); Taxol®, 12.5 mg/kg (■); Taxol, 25 mg/kg (□); 12.5 mg BrC16-paclitaxel/kg (▲); BrC16-paclitaxel, 25 mg/kg (Δ); BrC16-paclitaxel, 50 mg/kg (o); BrC16-paclitaxel, 100 mg/kg (♦). X-axis: number of days post-inoculation (L1210 cells); y-axis: percent survival.

Six-week old CB17 female SCID mice were inoculated (i.v.) with $5 \times 10^4$ L1210 (mouse leukemia) cells (day 0); BrC16-paclitaxel (12.5, 25, 50 or 100 mg/kg) or Taxol® (12.5 or 25 mg/kg) were then administered orally to the mice (9–10 mice/group) on days 1–5 post-inoculation. Stock drug formulations were diluted in PBS to reach the desired dosage level. Mice were checked daily, and survival times for each member of each group were determined. Results are presented in FIG. 12.

Example 15

Particle Size Analysis of BrC16-Paclitaxel/Pluronic-Containing Particles

Particles containing BrC16-paclitaxel and pluronic F68 (poloxamer 188, $HO(CH_2CH_2O)_{75}(CH(CH_3)CH_2O)_{30}(CH_2CH_2O)_{75}H$), at a 90 mole %/10 mole % ratio, were prepared by the procedures described hereinabove. Briefly, 48 mg of the paclitaxel derivative and 40 mg of the pluronic were dissolved in 0.2 ml of ethanol; 0.1-ml aliquots of the resulting solution were then slowly added to test tubes containing 2 ml of phosphate-buffered saline (PBS, 10 mM phosphate/150 mM saline, pH 7). The resulting two-ml suspensions were then combined into a single suspension of 4-ml volume.

This suspension was passed through a 5-micron filter, and the resulting filtrate subjected to particle size analysis using a Nicomp Model 370 submicron particle sizer. Results (nm,±std. deviation) by Gaussian analysis were: 44±17 (number weighting); 70±27 (volume weighting) and, 105±40 (intensity weighting). This confirmed that stable particles could be formed using pluronics as the conjugate.

Example 16

Particle Size Analysis of BrC16-Paclitaxel/Cremophor®EL-Containing Particles

Particles containing BrC16-paclitaxel and Cremophor®EL (glycerol polyethylene ricinoleate) were prepared as described in Example 1 hereinabove. Briefly, 48 mg of the paclitaxel derivative were dissolved along with 44 mg of the glycerol polyethylene ricinoleate in 0.2 ml of ethanol; 0.1-ml aliquots of the resulting solution were then slowly added to test tubes containing 2 ml of phosphate-buffered saline (PBS, 10 mM phosphate/150 mM saline, pH 7). The resulting two-ml suspensions were then combined into a single suspension of 4-ml volume.

Figure 13:
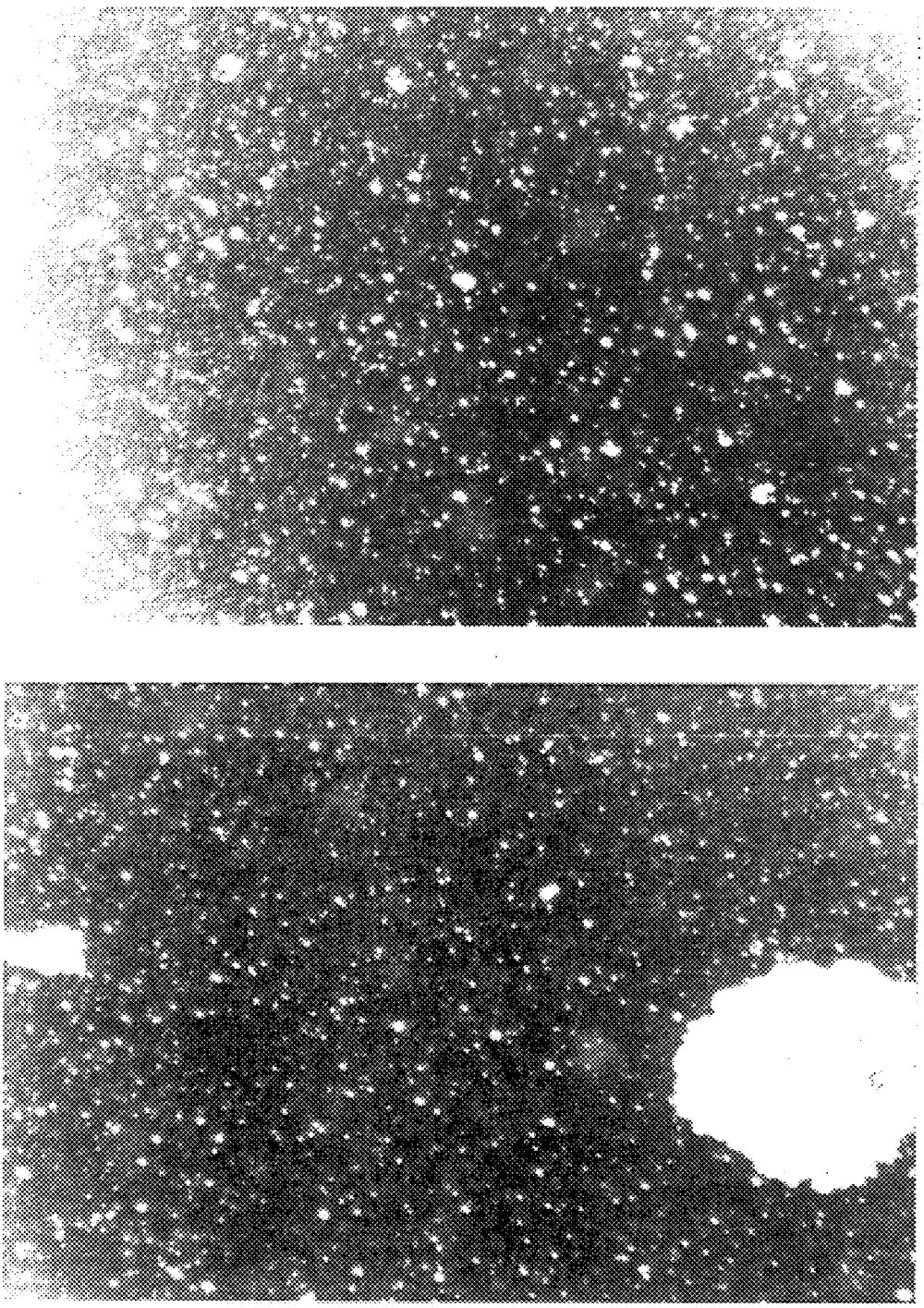
FIG. 13. Light Micrographs of BrC16-Paclitaxel/Cremophor®EL-Containing Particles.

This suspension was examined by Nomarski light microscopy (700×). Results are presented in FIG. 13. This confirmed that stable particles could be formed using glycerol polyethylene ricinoleate as the conjugate.

Example 17

Particle Size Analysis of BrC16-Paclitaxel/DOPE-GA-Containing Particles

DOPE-GA, also known as N-Glutaryl-PE, 18:1, is a phospholipid composed of 1,2-dioleoyl-sn-glycero-3-phosphoethanolamine conjugated to glutaric acid via an amide bond. Particles containing BrC16-paclitaxel and DOPE-GA, at a 50 mole %/50 mole % ratio, were prepared as described in Example 1 hereinabove. Briefly, approximately 48 mg of BrC16HTD and approximately 33 mg of DOPE-GA were dissolved in 0.26 ml of ethanol and 0.13 ml aliquots of this ethanolic solution were slowly added to test tubes containing 2 ml of HBS, (20 mM HEPES, 150 mM saline, pH 7.5). The resulting 2 ml suspensions were then combined to give a single volume of 4 ml.

The suspensions were blue-white in color and translucent. The 4 ml of suspension passed easily through a syringe filter with a nominal pore size of 5 microns. The filtrate was subjected to particle size analysis using a Nicomp Model 370 submicron particle sizer. Results (nm,±std. deviation) by Gaussian analysis were: 40±16 nm (number weighting); 67±27 nm (volume weighting) and 106±43 nm (intensity weighting).

Example 18

Hamycin/DSPE-PEG$_{2000}$-Containing Particles

Figure 14A:
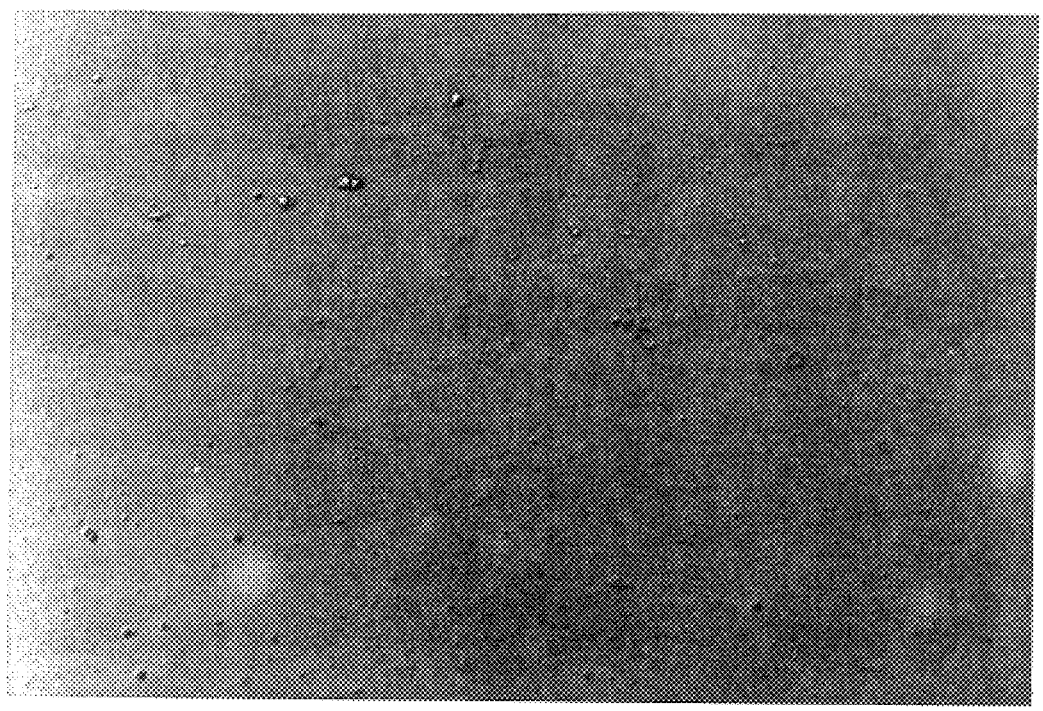
FIGS. 14A–14B. Light Micrographs using Nomarski optics of Hamycin-Containing Particles (A) 1 cm=27 µm; (B) 1 cm=13.6 µm.
Figure 14B:
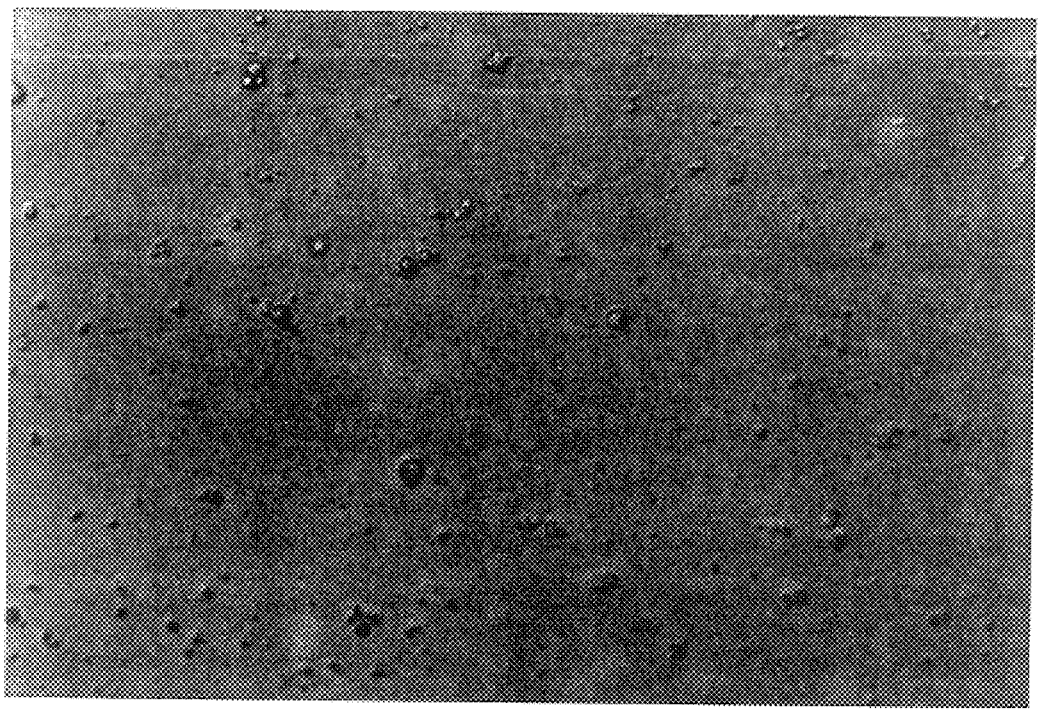

Hamycin/DSPE-PEG$_{2000}$ (20:80)(wt/wt) particles prepared according to Example 1 by the modified REV process were examined by light microscopy using Nomarski optics. The suspension contained a heterogeneous distribution of particles having diameters of less than 6 μm. The suspension was yellow in color and slightly opaque. FIG. 14 is a light micrograph of Hamycin/DSPE-PEG$_{2000}$ particles. One centimeter on the photo represents 27 μm in FIG. 14A and 13.6 μm in FIG. 14B.

Figure 15:
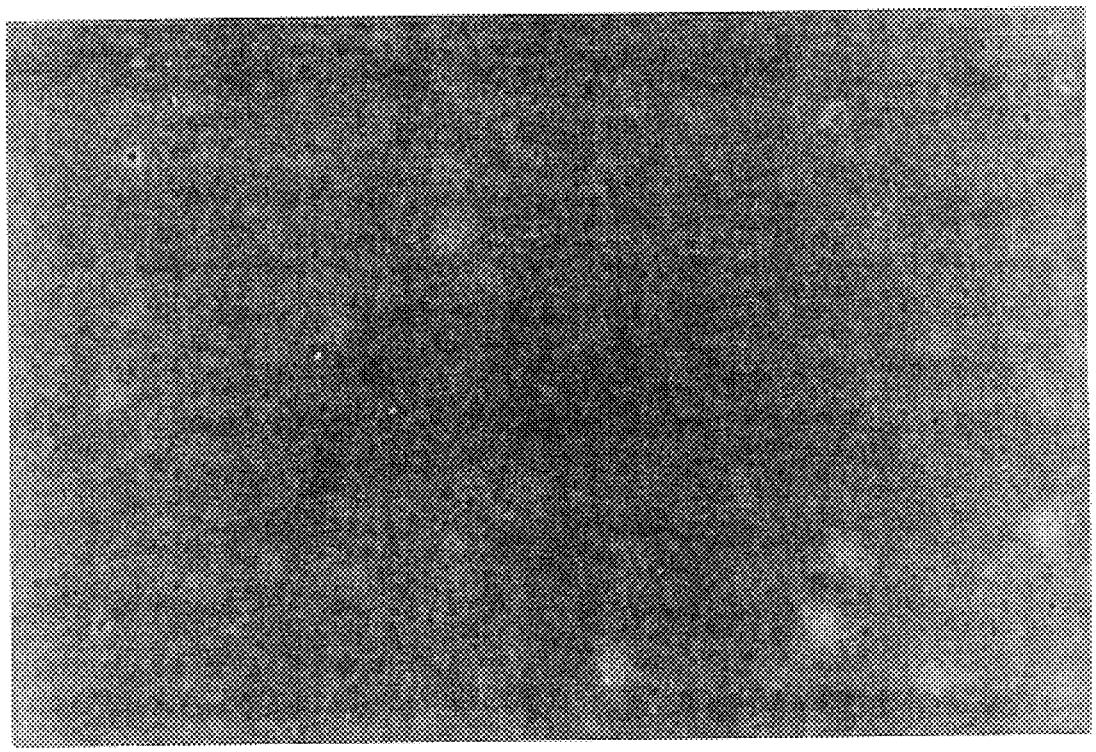
FIG. 15. Light Micrographs using phase contrast microscopy of Hamycin-Containing Particles. 1 cm=27 µm.

Hamycin/DSPE-PEG$_{2000}$ (80:20)(w/w) particles prepared by the dialysis method according to Example 1 were examined by phase contrast light microscopy. FIG. 15 is a light micrograph of Hamycin/DSPE-PEG$_{2000}$ (80:20) particles. One centimeter on the photo represents 27 μm. The suspension was yellow in color and translucent.

Particles were prepared by the dialysis method as described in Example 1. A suspension (4 ml) passed easily through a syringe filter with a nominal pore size of 5 μm. The filtrate was subjected to particle size analysis using a Nicomp Model 370 submicron particle sizer. These particles were relatively heterogeneous in size. As a result, the results of the Nicomp analysis suggested multiple populations of sizes. The sizes were determined either by Gaussian analysis or by Distribution analysis. Results (nm,±std. deviation) by Gaussian analysis were: 382±196 nm (number weighting); 205±105 nm (volume weighting) and 495±253 nm (intensity weighting). By distribution analysis, 66% of the particles were 105 nm and 34% were 398 nm (number weighting); 7% of the particles were 111 nm and 93% were 412 nm (intensity weighting) and 3% of the particles were 111 nm and 97% were 419 nm (volume weighting). The bimodal distribution found using distribution analysis suggests that there are larger particles (greater than 300 nm) present. In any case the size study indicated that particles do indeed form for Hamycin/DSPE-PEG$_{2000}$.

It is understood that the above description is intended to be illustrative and not restrictive. Many embodiments will be apparent to those of skill in the art upon reading the above description. The scope of the invention is not limited, therefore, solely to the above description, but should instead be determined by reference also to the appended claims, along with the full scope of equivalents to which such claims are entitled. The disclosures of all articles and references, including patent applications and publications, are incorporated herein by reference for all purposes.

What is claimed is:

1. A particle which comprises:
   (a) a core comprising a poorly hydrophilic compound wherein said core is substantially free of water and added oil such that the particle is neither a liposome nor an emulsion;
   (b) a conjugate of a biocompatible hydrophilic domain and a biocompatible hydrophobic domain, wherein said conjugate surrounds the core, wherein:
   the poorly hydrophilic compound comprises from about 20 mole % to about 99 mole % of the particle;
   the conjugate comprises from about 1 mole % to about 80 mole % of the particle; and
   the particle has a diameter of at least about 15 nm,
   wherein the particle is formed by an injection technique using a solvent that is miscible with water,
   wherein the injection technique comprises:
   (i) combining the poorly hydrophilic compound, the conjugate of the biocompatible hydrophilic domain and the biocompatible hydrophobic domain in a solvent that is miscible with water to form a mixture or solution,
   (ii) injecting the mixture or solution formed in (i) into an aqueous solution to form the particles, and
   (iii) collecting the particles.

2. The particle of claim 1, wherein the compound is selected from the group consisting of bisintercalating antibiotics, macrolides, nucleoside antibiotics, DNA intercalators, antiestrogens, steroidal compounds, taxanes, vinca alkaloids, bryostatins, cephalosporins, rifamycins, mitomycins, bleomycins, and camptothecins.

3. The particle of claim 2, wherein the taxane is paclitaxel.

4. The particle of claim 1, wherein the poorly hydrophilic compound comprises a compound covalently attached to a hydrophobic domain selected from the group consisting of acyl chains, hydrophobic peptides and hydrophobic polymer chains.

5. The particle of claim 4, wherein the hydrophobic domain is an acyl chain.

6. The particle of claim 5, wherein the acyl chain has the formula

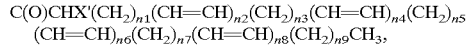

and wherein:
n1 is equal to zero or an integer of from 1 to 21;
n3 is equal to zero or an integer of from 1 to 18;
n5 is equal to zero or an integer of from 1 to 15;
n7 is equal to zero or an integer of from 1 to 12;
n9 is equal to zero an integer of from 1 to 9;
each of n2, n4, n6 and n8 is independently equal to 0 or 1;
the sum of n1+2n2+n3+2n4+n5+2n6+n7+2n8+n9 is an integer equal to from 3 to 21; and,
$X^1$ is H or a hydrolysis-promoting group.

7. The particle of claim 6, wherein the acyl chain has the formula —C(O)CHX$^1$(CH$_2$)$_{n1}$CH$_3$.

8. The particle of claim 7, wherein the acyl chain is —C(O)CHX$^1$(CH$_2$)$_9$CH$_3$, —C(O)CHX$^1$(CH$_2$)$_{11}$CH$_3$ or —C(O)CHX$^1$(CH$_2$)$_{13}$CH$_3$.

9. The particle of claim 8, wherein $X^1$ is a hydrolysis-promoting group.

10. The particle of claim 9, wherein the hydrolysis-promoting group is selected from the group consisting of F, Cl, Br, I, —$OC_6H_4X_2$ and —$C(O)X^2$, wherein $X^2$ is F, Cl, Br, I, CN, $NO_2$ or $NH_3^+$.

11. The particle of claim 10, wherein the hydrolysis-promoting group is Br.

12. The particle of claim 1, wherein the poorly hydrophilic compound comprises an acyl chain selected from the group consisting of —$C(O)CHBr(CH_2)_9CH_3$, —$C(O)CHBr(CH_2)_{11}CH_3$, or —$C(O)CHBr(CH_2)_{13}CH_3$ attached to paclitaxel.

13. The particle of claim 1, wherein the conjugate hydrophobic domain comprises the acyl chain region of an amphipathic lipid.

14. The particle of claim 13, wherein the amphipathic lipid is a phosphatidylethanolamine.

15. The particle of claim 14, wherein the phosphatidylethanolamine is distearoyl phosphatidylethanolamine (DSPE).

16. The particle of claim 1, wherein the conjugate hydrophobic domain is a hydrophobic polymer.

17. The particle of claim 16, wherein the hydrophobic polymer is a silicon polymer or poly(oxypropylene).

18. The particle of claim 1, wherein the conjugate hydrophilic domain is a hydrophilic polymer.

19. The particle of claim 18, wherein the hydrophilic polymer is selected from the group consisting of polyethylene glycols, celluloses, hydrophilic peptides, polysaccharides, polyethylene oxides, polyacrylic acids, polyacrylamides and polyvinyl pyrrolidinones and polymethacrylates.

20. The particle of claim 19, wherein the hydrophilic domain is a polyethylene glycol (PEG) or a polyethylene oxide having a molecular weight of from about 50 to about 5000.

21. The particle of claim 1, wherein the conjugate is DSPE-PEG$_{2000}$.

22. The particle of claim 1, wherein the conjugate comprises at least one charged lipid.

23. The particle of claim 22, wherein the charged lipid has a net negative charge.

24. The particle of claim 23, wherein the negatively charged lipid is DOPE-GA.

25. The particle of claim 22, wherein the charged lipid has a net positive charge.

26. The particle of claim 1, wherein the conjugate is a copolymer having the formula $HO(CH_2CH_2O)_a(CH(CH_3)CH_2O)_b(CH_2CH_2O)_cH$, a and b are each independently equal to integers of from about 10 to about 100 and c is equal to zero or is an integer of from about 1 to about 100.

27. The particle of claim 26, wherein a and c are each equal to an integer of about 75 and b is equal to an integer of about 30.

28. The particle of claim 1, wherein the conjugate is glycerol polyethylene glycol ricinoleate.

29. The particle of claim 1 having a diameter of up to about 10,000 nm.

30. The particle of claim 29 having a diameter of from about 15 nm to about 200 nm.

31. The particle of claim 1, wherein the hydrophobic compound comprises greater than about 50 mole % of the particle and the conjugate comprises less than about 50 mole % of the particle.

32. The particle of claim 31, wherein the hydrophobic compound comprises from about 80 mole % to about 99 mole % of the particle and wherein the conjugate comprises from about 1 mole % to about 20 mole % of the particle.

33. The particle of claim 1 comprising: (a) from about 80 mole % to about 99 mole % of paclitaxel covalently attached to —$C(O)CHBr(CH_2)_9CH_3$, —$C(O)CHBr(CH_2)_{11}CH_3$, or —$C(O)CHBr(CH_2)_{13}CH_3$; and, (b) from about 1 mole % to about 20 mole % of a conjugate selected from the group consisting of DSPE-PEG$_{2000}$, DOPE-GA, $HO(CH_2CH_2O)_{75}$$(CH(CH_3)CH_2O)_{30}(CH_2CH_2O)_{75}H$ and glycerol polyethylene glycol ricinoleate, wherein the particle has a diameter of from about 15 nm to about 200 nm.

34. The particle of claim 33 comprising DSPE-PEG$_{2000}$ and paclitaxel attached to —$C(O)CHBr(CH_2)_{13}CH_3$.

35. A composition comprising the particle of claim 1 and a pharmaceutically acceptable carrier.

36. A method of administering a compound to an animal which comprises administering to the animal the composition of claim 35, wherein the method of administration is nasal, oral, ophthalmic, topical, transdermal, vaginal, rectal, intrathecal, subcutaneous, intramammary, intraperitoneal, intravenous, intratumoral, intracavity, intramuscular or intra-arterial.

37. The method of claim 36, wherein the animal is a human.

38. The method of claim 37, wherein the administration comprises oral, intravenous or intraperitoneal administration.

39. The particle of claim 1 wherein the core hydrophobic compound is a derivative of a non hydrophobic compound, said derivative compound comprising a compound attached to a biocompatible hydrophobic domain.

40. The particle of claim 1, wherein the compound is selected from the group consisting of benzonaphthopyranone, pyrrolo[1,4]benzodiazepines, bisindolealkaloids, etoposide, teniposide, bis(benzimidazoles) and adenine arabinoside.

41. The particle of claim 5, wherein the acyl chain is branched.

42. The particle of claim 5, wherein the acyl chain is straight.

43. The particle of claim 5, wherein the acyl chain is saturated.

44. The particle of claim 2, wherein the compound is a taxane.

45. The particle of claim 5, wherein the acyl chain is unsaturated.

46. The particle of claim 5, wherein the acyl chain has the formula

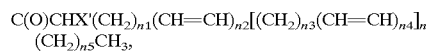

and wherein:

n1 is equal to zero or an integer of from 1 to 21;

n3 is equal to zero or an integer of from 1 to 18;

n5 is equal to zero or an integer of from 1 to 15;

n is equal to zero or an integer of from 0 to 21 each of n2 and n4 is independently equal to 0 or 1;

the sum of n1+2n2+n+n5 an integer equal to from 3 to 21; and, $X^1$ is H or a hydrolysis-promoting group.

47. The particle of claim 1, wherein the solvent is ethanol.

48. A particle of claim 1, wherein the poorly hydrophilic compound is selected from the group consisting of anti-cancer agents, anti-inflammatory agents, and anti-microbial agents.

49. A composition comprising the particle of claim 48 and a pharmaceutically acceptable carrier.

50. A method of administering a therapeutically effective amount of the composition of claim 49 to a mammal, wherein the mammal is afflicted with a disorder selected from the group consisting of cancers, inflammatory disorders and microbial infections, wherein the compound is therapeutically effective against the disorder, and wherein the method of administering is nasal, oral, ophthalmic, topical, transdermal, vaginal, rectal, intrathecal, subcutaneous, intramammary, intraperitoneal, intravenous, intratumoral, intracavity, intramuscular or intra-arterial.

51. The method of claim 50, wherein the disorder is a cancer, the poorly hydrophilic compound is BrC16-paclitaxel and the conjugate is DSPE-$PEG_{2000}$.

52. The method of claim 51, wherein the particle is from at least about 15 nm to about 200 nm in size and wherein the particle comprises from about 80 mole % to about 99 mole % of BrC16-paclitaxel and from about 1 mole % to about 20 mole % of DSPE-$PEG_{2000}$.

* * * * *